(12) United States Patent
Pinto et al.

(10) Patent No.: US 7,067,648 B2
(45) Date of Patent: Jun. 27, 2006

(54) REGULATORY SEQUENCES OF THE MOUSE VILLIN GENE—USE IN TRANSGENESIS

(75) Inventors: Daniel Pinto, Bagnolet (FR); Sylvie Robine, Vanves (FR); Frédéric Jaisser, Malakoff (FR); Daniel Louvard, Sceaux (FR)

(73) Assignees: Institut Curie (FR); Centre National de la Recherche and Scientifique (FR)

( * ) Notice: Subject to any disclaimer, the term of this patent is extended or adjusted under 35 U.S.C. 154(b) by 0 days.

(21) Appl. No.: 09/877,935

(22) Filed: Jun. 8, 2001

(65) Prior Publication Data

US 2002/0102705 A1  Aug. 1, 2002

Related U.S. Application Data

(63) Continuation of application No. PCT/EP98/08009, filed on Dec. 9, 1998.

(51) Int. Cl.
C07H 21/04 (2006.01)
(52) U.S. Cl. .................................... 536/24.1; 536/24.5
(58) Field of Classification Search ............... 536/23.1, 536/24.1
See application file for complete search history.

(56) References Cited

FOREIGN PATENT DOCUMENTS

EP         0 496 174 A1    7/1992

OTHER PUBLICATIONS

GenBank Accession No. M98454.
Aronow et al., "Functional Analysis of the Human Adenosine Deaminase Gene Thymic Regulatory Region and Its Ability To Generate Position-Independent Transgene Expression," *Mol. Cell. Biol.*, 1992, 12(9):4170-4185.
Bacchi and Gown, "Distribution and Pattern of Expression of Villin, A Gastrointestinal-Associated Cytoskeletal Protein, in Human Carcinomas: A Study Employing Paraffin-Employing Paraffin-Embedded Tissue," *Lab. Invest.*, 1991, 64(3):418-424.
Becker, "The Establishment of Active Promoters in Chromatin," *BioEssays*, 1994, 16(8):541-547.
Bisaha et al., "Characterization of an Enhancer Element in the Human Apolipoprotein C-III Gene That Regulates Human Apolipoprotein A-I Gene Expression in the Intestinal Epithelium," *J. Biol. Chem.*, 1995, 270(34):19979-19988.
Boller et al., "Differential distribution of villin and villin mRNA in mouse intestinal epithelial cells," *Differentiation*, 1988, 39:51-57.
Breathnach and Chambon, "Organization and Expression of Eucaryotic Split Genes Coding for Proteins," *Ann. Rev. Biochem.*, 1981, 50:349-383.

Bry et al., "Paneth cell differentiation in the developing intestine of normal and transgenic mice," *Proc. Natl. Acad. Sci. USA*, 1994, 91:10335-10339.
Carboni et al., "Characterization of Intestinal Brush Border Cytoskeletal Proteins of Normal and Neoplastic Human Epithelial Cells," *Am. J. Path.*, 1987, 129(3):589-600.
Cartier et al., "Establishment of renal proximal tubule cell lines by targeted oncogenesis in transgenic mice using the L-pyruvate kinase-SV40 (T) antigen hybrid gene," *J. Cell Science*, 1993, 104:695-704.
Cheng and LeBlond, "Origin, Differentiation and Renewal of the Four Main Epithelial Cell Types in the Mouse Small Intestine," *Am. J. Anat.*, 1974, 141:461-479.
Cohen-Tannoudji et al., "I-*Sce*I-Induced Gene Replacement at a Natural Locus in Embryonic Stem Cells," *Mol. Cell. Biol.*, 1998, 18(3):1444-1448.
Cohn et al., "Use of Transgenic Mice to Map *cis*-acting Elements in the Intestinal Fatty Acid Binding Protein Gene (*Fabpi*) That Control Its Cell Lineage-specific and Regional Patterns of Expression along the Duodenal-Colonic and Crypt-Villus Axes of the Gut Epithelium," *J. Cell. Biol.*, 1992, 119:27-44.
Crossman et al., "The Mouse Ileal Lipid-binding Protein Gene: A Model for Studying Axial Patterning during Gut Morphogenesis," *J. Cell Biol.*, 1994, 126(6):1547-1564.
Cui et al., "Reporter genes in transgenic mice," *Trans. Res.*, 1994, 3:182-194.
Dunbar et al., "Functional analysis of the mouse villin gene promotor," *Mol Biol. Cell*, 1998, 9(Suppl.):1840.
Efrat et al., "Beta-cell lines derived from transgenic mice expressing a hybrid insulin gene-oncogene," *Proc. Natl. Acad. Sci. USA*, 1988, 85:9037-9041.
Ezzell et al., "Differential localization of villin and fimbrin during development of the mouse visceral endoderm and intestinal epithelium," *Development*, 1989, 106:407-419.
Fearon and Vogelstein, "A Genetic Model for Colorectal Tumorigenesis," *Cell*, 1990, 61:759-767.

(Continued)

*Primary Examiner*—Celian Qian
(74) *Attorney, Agent, or Firm*—Fish & Richardson P.C., P.A.

(57) ABSTRACT

The invention relates to regulatory sequences of the mouse villin gene that efficiently drive transgenic expression in immature and differentiated epithelial cells of the intestine and uro-genital tracts. The invention also relates to recombinant constructs comprising said regulatory sequences, for the control of the targeted expression of determined nucleic acid sequences so-called (heterologous sequences or also transgenes), in cells or tissues originating from the intestinal mucosa. A further object of the invention is to provide cells, tissues or organisms including animals, expressing said determined nucleic acid sequences in a targeted manner.

16 Claims, 16 Drawing Sheets

OTHER PUBLICATIONS

Figure 1:
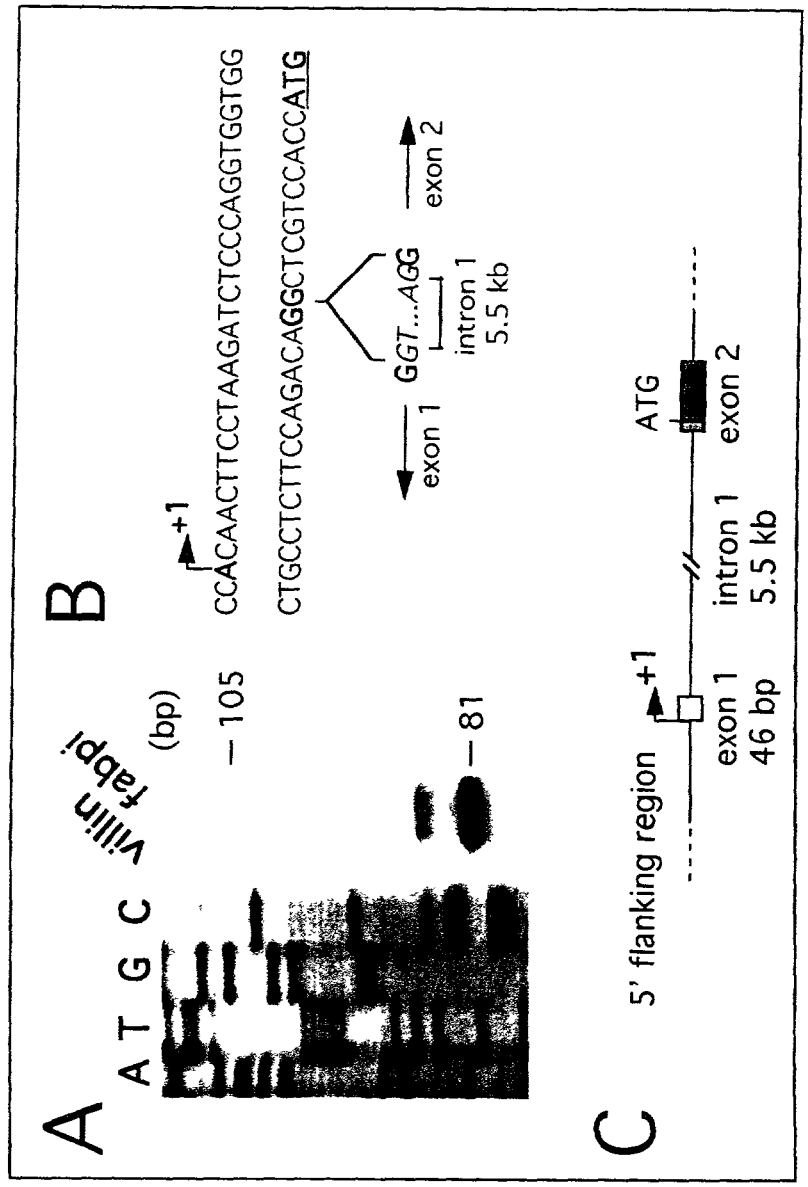

Gordon and Hermiston, "Differentiation and self-renewal in the mouse gastrointestinal epithelium," *Curr. Opin. Cell Biol.*, 1994, 6:795-803.

Green et al., "The Mouse Intestinal Fatty Acid Binding Protein Gene: Nucleotide Sequence, Pattern of Developmental and Regional Expression, and Proposed Structure of Its Protein Product," *DNA Cell Biol.*, 1992, 11:31-41.

Hall et al., "Regulation of cell number in the mammalian gastrointestinal tract: the importance of apoptosis," *J. Cell Science*, 1994, 107:3569-3577.

Hanahan, "Dissecting Multistep Tumorigenesis in Transgenic Mice," *Annu. Rev. Genet.*, 1988, 22:479-519.

Hauft et al., "Expression of SV-40 T Antigen in the Small Intestinal Epithelium of Transgenic Mice Results in Proliferative Changes in the Crypt and Reentry of Villus-associated Enterocytes into the Cell Cycle but Has No Apparent Effect on Cellular Differentiation Programs and Does Not Cause Neoplastic Transformation," *J. Cell Biol.*, 1992, 117(4):825-839.

Hermiston et al., "Chimeric-transgenic mice represent a powerful tool for studying how the proliferation and differentiation programs of intestinal epithelial cell lineages are regulated," *Proc. Natl. Acad. Sci. USA*, 1993, 90:8866-8870.

Hermiston and Gordon, "In Vivo Analysis of Cadherin Function in the Mouse Intestinal Epithelium: Essential Roles in Adhesion, Maintenance of Differentiation, and Regulation of Programmed Cell Death," *J. Cell Biol.*, 1995, 129(2):489-506.

Kim et al., "Transgenic Mouse Models That Explore the Multistep Hypothesis of Intestinal Neoplasia," *J. Cell Biol.*, 1993, 123(4):877-893.

Kistner et al., "Doxycycline-mediated quantitative and tissue-specific control of gene expression in transgenic mice," *Proc. Natl. Acad. Sci. USA*, 1996, 93:10933-10938.

Markowitz et al., "The human sucrase-isomaltase gene directs complex patterns of gene expression in transgenic mice," *Am. J. Physiol.*, 1993, 265(3):G526-G539.

Maunoury et al., "Villin expression in the visceral endoderm and in the gut anlage during early mouse embryogenesis," *EMBO J.*, 1988, 7(11):3321-3329.

Maunoury et al., "Developmental regulation of villin gene expression in the epithelial cell lineages of mouse digestive and urogenital tracts," *Development*, 1992, 115:717-728.

Moll et al., "Villin: a cytoskeletal protein and a differentiation marker expressed in some human adenocarcinomas," *Virchows Arch B*, 54:155-169.

Perret et al, "DNase I-hypersensitive sites are associated, in a tissue-specific manner, with expression of the calbindin-D9k-encoding gene," *Gene*, 1991, 108:227-235.

Pinto et al., "Regulatory Sequences of the Mouse Villin Gene That Efficiently Drive Transgenic Expression in Immature and Differentiated Epithelial Cells of Small and Large Intestines," *J. Biol. Chem.*, 1999, 274(10):6476-6482.

Ponder et al., "Derivation of mouse intestinal crypts from single progenitor cells," *Nature*, 1985, 313:689-691.

Potten and Loeffler, "Stem cells: attributes, cycles, spirals, pitfalls and uncertainties—Lessons for and from the Crypt," *Development*, 1990, 110:1001-1020.

Pringault et al., "Structure of the human villin gene," *Proc. Natl. Acad. Sci. USA*, 1991, 88:10811-10815.

Robine et al., "Can villin be used to identify malignant and undifferentiated normal digestive epithelial cells?" *Proc. Natl. Acad. Sci. USA*, 1985, 82:8488-8492.

Robine et al., "Regulatory Sequences on the Human Villin Gene Trigger the Expression of a Reporter Gene in a Differentiating HT29 Intestinal Cell Line," *J. Biol. Chem.*, 1993, 268(15):11426-11434.

Robine et al., "Gene Targeting in Epithelial Cells of the Endodermal Cell Lineage Using the Human Villin Promoter," *Cell Biol. Intl.*, 1994, 18(5):471.

Robine et al., "Epithelial Cell Growth and Differentiation—IV. Controlled spatiotemporal expression of transgenes: new tools to study normal and pathological states," *Am. J. Physiol.*, 1997, 273(4):G759-G762.

Rottman and Gordon, "Comparison of the Patterns of Expression of Rat Intestinal Fatty Acid Binding Protein/Human Growth Hormone Fusion Genes in Cultured Intestinal Epithelial Cell Lines and in the Gut Epithelium of Transgenic Mice," *J. Biol. Chem.*, 1993, 268(16):11994-12002.

Sabourin et al., "An Intronic Enhancer Essential for Tissue-specific Expression of the Aldolase B Transgenes," *J. Biol. Chem.*, 1996, 271(7):3469-3473.

Schmidt et al., "Cell Migration Pathway in the Intestinal Epithelium: An In Situ Marker System Using Mouse Aggregation Chimeras," *Cell*, 1985, 40:425-429.

Simon et al., "A 20-nucleotide element in the intestinal fatty acid binding protein gene modulates its cell lineage-specific, differentiation-dependent, and cephalocaudal patterns of expression in transgenic mice," *Proc. Natl. Acad. Sci. USA*, 1995, 92:8685-8689.

Simon et al., "Suppressor and Activator Functions Mediated by a Repeated Heptad Sequence in the Liver Fatty Acid-binding Protein Gene (*Fabpl*)," *J. Biol. Chem.*, 1997, 272(16):10652-10663.

Sweetser et al., "Transgenic mice containing intestinal fatty acid-binding protein-human growth hormone fusion genes exhibit correct regional and cell-specific expression of the reporter gene in their small intestine," *Proc. Natl. Acad. Sci. USA*, 1988, 85:9611-9615.

Tremp et al., "Induction of a lesion resembling human thymoma in transgenic mice," *Proc. Am. Assoc. Cancer Res.*, 1993, 34:A3180.

West et al., "Localization of Villin, a Cytoskeletal Protein Specific to Microvilli, in Human Ileum and Colon and in Colonic Neoplasms," *Gastroenterology*, 1988, 94:343-352.

Wright and Irwin, "The kinetics of villus cell populations in the mouse small intestine," *Cell Tissue Kinet.*, 1982, 15:595-609.

Genomic sequence of the mouse villin gene regulatory sequences

```
GATCTGGTGC ACCAAGGACA CTGTGGTCCC AGCACTGGGG AGGTGGAGGG AGGAGGGTCA 60
GAAGTTTAAG GTCATCCTTG GTTACATAGC AAGGTTTCAG CCAGCTTCAG CTACATGAAA 120
CCTTTGTTTG TTTGTTTGTT TGTTTTAAAG CATTAATAAA TAATACCATA AGGAGGTTGG 180
CAGTGGTGGC AGACACCTTT AATTCCAGTA TTCAGGAGGC AGAAGCAGGC AGATCTCTGT 240
GAGTTCGAAG TCAGCCTAGT CTGCAAAGCT AGTTCCAGGA TGGCAAGGGC TACACAGAGA 300
AACCTTGTCT CATAAAACCA AAGTAGTAGT AGTAGTAGTA ATGCCATAGA GAAAATTGGA 360
GTCCATTCAG GATGGACCAT CCTATAAGAT GATTCTCTTG ACCCAGGTAA GCTAATGTCA 420
TGGGGAAAGG GGATGGGACT GTCCTAGATT AAAAAGTGCT GAGGCGATGC CTATTCTCAA 480
TTTGATTCCA TATGAAAAGG CTGATAAGGC CAAGAGAAG TGGAACTGGG ACTCTGGACT 540
GAAGACGTGA CGGCCTTATA AACACTGGCA CTTATAAACA CTTATAAACA CTGGCACAGG 600
CGTTCAGGTT TGAAGATCAC TTTCAAACCA CAGAACAGAA AGTGCTCGCT CGTCCTCAGC 660
GTAGCGAGCA CTGGCTGCAG AAGAGTGATA TTTAGTGAAA GCTACCTTCA CAATATCTTT 720
GCACTTATCA CATACACGTG TCAAATGTGC TAACTCCCTA GTCCACAGAT GGCTGTTACA 780
CTCGTTTCTG CTTTCCCATC TGGTTGACAT TTGTCAGAAC CAGAAATTAG AAATGTGGGT 840
ATTTATTTGT GTGCTGAGGA CACCATCCAG GGCTTTTCAC ATTTCAGGCA CATGGTTTAC 900
TAACTGGGCT ACTTCTCCAA CGGTTTGAAA CCATTTGTTT TATATTTACT TATTTTGTGT 960
GCATGAGGTA GGCATGTATA CGTATGTATA GGAGTCATGC ATGTGGCTGC TACCCTCAAA 1020
ATCATTGCAG ATCCCCAGCA AGTGAAGTCA CCGAGCGTTG TAAGTTGTTA TGTGGGACTG 1080
GGAGCCAAGG CTGGGTTCTC TGCAAGAGCA GCCAGTGGCC TTAACCATGG GACCAGCTCT 1140
CTAGGCCTAA GGTAATCTTT AGTTTTTTAA AAATATATAT TCTCAGCCGG GTGTGGTGGC 1200
ACACGCCTTT AATCCCAGCA CTTGAGAGGC TGAGGTGTAG GAATTATACA CACAGGCCAG 1260
CTGGGGTGCA GAGCTTGGCC CTGTTTTTTT TGTTTTTTCT TTATGTGCAC TGGTGTCTTA 1320
CCTGCGTGTA TGTCCGTGCA AGGGTGTCAG ATCCCTTGGA GCTGGAGTTA AAGACAGTTG 1380
TGATCACGCT GCCGTTACAG ATGCTGGAAA TTGAACCCAG GTGTCCCTAG AGAAGCAGCC 1440
AGTGCTCTTA ACTTCTGAGC CACCCCTCCA ACCCTGCTTT TAGAGACTCT TAACCTTTTG 1500
TGTAATGTGG GAACTGAGTG GATCTTGCAC TTACCAAGTG TGTGCTGCGC TGTAGCATCA 1560
CTGAGCCCGT ACCCACACGA CTAGTGGATA CAGTTTAAGG GCAAACACTT AACAATGACA 1620
ATAGTTGGAT AGAGTTTGAA TATAGTCCTG AGCTATTGGT TAGCGTGACC TTTGCTGTCC 1680
TTAGCATGTG CTGTGAGAAG ATAGAAAAAT GAAGACTTGA GTCTAGTCCT GGAACCCACA 1740
GAGGCAGGCG AGAACCCACT CCTGAAAGTT GTTCTCTGAG CTTCACATAC AACTTCACAT 1800
```

FIGURE 6A

```
AATAGTTACA ATGATAATAA TAATTAGTAA ATTCTTTTAA AAGGTATATG TTGGGAGGGA 1860
GAGATGGCTC AGCTTCCAGG AGCACTTGCT GCTCTTGCAG AGGACCTAGA TTCAGTTCCC 1920
AGGACTCATA TGGTGGCTCA CAGCCATCTG TAAATCCAGT TCCAGAGGGT TCCACACCCT 1980
CTTCTGGCCT CCACAGGCAC CACATACATA GTACACAGAC ATACATGCAG GCAAAACACC 2040
CATACACACA TAAATAAATA AGGAAACTTA AAAGGTGCAT GTGTTGGTAA ACATTGTGCT 2100
TACACATGCT GATTGAAGAC ATGTACAACG CACACACTGA AGAGGGATCT GGGGCTGGAG 2160
AGATGGCTCA GCGGTTAAGA GCACTGACTG CTCTTCCGAA GGAAGGTCCT GAGTTCAAAT 2220
CCTAGCAACC ACATGGTGGC TCACAACCAT CCATAATGAG ATCTGACACC CTCTTCTGGT 2280
GCATCTGAAG ACAGCTGCAG AGCTACAGTG TACTTAGATA TACTAATAAA TAAATCTTTT 2340
TTTAAAAAAA TGAAGAGGGA TCTGAGACAC CTCAAAGAG ATTATGAGCA GTGACTCACG 2400
GGTGATTATC TATCCTGGAG TTTTTCCTTT CCGCTTGGCT TGCAACTGGG TGGACAGACG 2460
CCCCTTTTCA TTCACAAGAA CGGGTGCTAC ATTATTTCTG AACAAAACAG CACCTGCAGT 2520
ATGTTTACTG TCCTTGCTGA CTATGAGCAC GCGCACGCGC GCGCACAC ACACACAC 2580
ACACACACAC ACACACACAC ACACACACAC ATTCAGTCTC CAGAGCTCTT GGGAAGGTCA 2640
AGAAGAGGCT GCCCTCAAAC ACGATCTTCA TCTTTCCCTC CTAAAGGAGA CCACGATTCC 2700
AAGGTGGCAG AAGATCTACA GGGGGCAGAG GCAGGGAGGG GGAAGCAGGC CATGGTTTCC 2760
AGAGACCTAC AGCAGAGGGC AGCAAGGCAG ATCCCCAGGT CCAGGGCAGG GAGGTGGAGG 2820
CCCTTGTTCC GAGGAGAAGG CAGGCGGCAG AACAGGGTTC AAAGGCACAG GTTTATGGCA 2880
GCTCATAAAA GTGGAGGTCG TGGCTCACTC AGAAAGGAGG AAGAAGGGAA AGGCCCTTGT 2940
GCCCACTGAG CGAGGGTCAT GCTGAGTAGG AGAGATCTGC AGGGGTGCCA GGAGCCCCAC 3000
CTGTCTGTCC CAAGGGAACC CCAAGTGTGA ACTCTGGCCT TGGGTGCTGA GTTCCAGCTA 3060
CAAGACCCCA GGAGTCCTAC TCCATCCCCA TCCAGTGCCC CCTCGCCCCG CCACACCCCA 3120
CCCCCGACTC CCGTGCCACT TCTCTAGGGC TGGAGGGTGG CCAGCCCTGG TGGGGGTTGC 3180
CTACCTGCAG GTAGAGCCCA GGTCCTAGCC GGAAGTGCAC CCCATCCCTG AAGCTGCAGA 3240
GCCAAGGGCG GGCACACGG CAGCTCAGGC TGTCAGGCTG TTGCTGGGCT CTAGGTTCCC 3300
AGGGACCTGG GCACCTACTT CCCCACCCCC CCATCCATTC TCTCTGGGGC CCTATCTTCC 3360
CTTATATGGT GAAGGAAGTT CCTGGGGGGG GGGGTGGTG GTGAGGACAA AGGTCGTTCG 3420
GTCTCCTGCA GCCAGCTTGC CACAACTTCC TAAGATCTCC CAGGTGGTGG CTGCCTCTTC 3480
                                 +1            exon 1
                    (transcription start site)
CAGACAGGTA AGGCAATTGG GTGGGACAC ATGGTGACCA CAGGTGGTTG GAGGGGACAG 3540
GGTCCTTGCT TCTCTCTGGC AGCCTGTGCT TTCTGTAGCA CCTTGGTATA AGTTTGGGGG 3600
```

FIGURE 6B

```
TGAGGTAAGG TGCTCTGAAA CTCTGAAAGA AGCAAGAAGC CAGCAGGCTG TCTTGGGCCT 3660
TCAATGAAGG AAGTTCACAG ACCCCCTTTC CTGTAAGTCA CCTTCGCTTC ATCTGTGTAG 3720
ATTCCCTGGG ACCAAGGTGG CTCCTGGGAC TCAGATTTCT ACAATTAAAA TCAGGACAGT 3780
CCTGAGACTT GGACTCCGTG CCTGTATTTA CTACTTCTCT CTGGCTGCTC ATTTCTGTGT 3840
TCATGTCTTA CACATCTGAA ATGGTTTCTT TGTGTCACCA TTCCCCTGAC ACTCCTGGGA 3900
GGTCGTATCC TTGGCACATG TATCCTGGGA TGTAAGCTGC AGCCACCAGG AGAGAGGGGG 3960
AGAGTCAGGA GCTGTGTCCT AGGCCCTATT AGGCCTGGAC ATCACCCCTT TCCTAGAAAT 4020
GGCCCCTCCA TTTTTCGGTT ACCATGATCT ATTTTATATC AGAGTGGGCA GTGAAAGCCA 4080
AACCTGCCCA GAAGTTTGGG ACTCACTCAG ACCAAGGTTA TCTGCTCAGA AATCCCCCTG 4140
TCACTTGAGG TTGGGAGAAT CTGCCTCTGG GGGCTTCCAG GTCTTGGTTA GCAGGAGGGT 4200
ATCCTTTGTA TAGGGCATGA CCTAGTCTAT GGTGTTACTA CATTCCTGTC CAGTTAAAAG 4260
CTGGAACTAA AACCCACGGC AGCGCCCAGG ATTCTCTACA GTTGTACCCC AAGAACAACA 4320
AGACAGTAGA TATGCAAGGA TAGGTAGCTG GGGAGAAGAA GAACTTAAAC CCCCCCAAAG 4380
GCCCACAGGT TCCGTTCCCT AGTTCACAAT GCCAGTATGA GTGCTAGCTA CTATGGGCTG 4440
TGAGTTGGTA GCTACAAGCA TGAGTGATGT TCATGTGTGT AGTGTGTATA ATCTGAGCAC 4500
TTGGGAGGCT GAAGCAGGAG GATTGCTATA TGTTTGAGGC CAGCCTGAGC TATAGAGCGA 4560
GACTTTGTCT TTAAGAAAAA AATGAAAGCC CAGCAGTGGT GGCACACGCC TTTAATCCCA 4620
GCACTTGGGA GGCAGAAGCA GGCAGATTTC TGAGTTCAAG GCCAGCCTGG TCTATAGAGT 4680
GAGTTCCAGG ACAGCCAGGG CTACACAGAG AAACCCTGTT TTGAAAAACC AGAAAAACAA 4740
AACAAAACAA AACAAAACAA AACCCAAACC CAAACCCAAA CCTCTCATCT CTCATCTCTC 4800
TAGGCTGTGT CTGTCTAGGT GGTAGAGTTT GGGGACTTCA GACTTATATA TAAATAGGCC 4860
TTTTTATCAC TGGTCAGAGA CGAGAAAGGT TTCAGTCTGG GACACAGTGG GACCCTGAGA 4920
AAGTACTCCT TGCCAGCCCA AAAATTCTGG GAAGGCTTCC TGGAGGAAGT GTGTCCCGAT 4980
CAGACTACTG TTCTAGAAGG CAGAAGAGAG GGTTGGAAGA ATGTTGGTGG ACAGACAGTT 5040
GGAACAGAAG GACAGGAGGG GGAGGCATCC AAGATTCTGA ACATGTAGCT GACTTTTGGT 5100
TCTCTGGGTG ACAAGTGTCC CCCAGGGATA GGGCTGTAGA AAGGGGACCA GGGGTGAGCC 5160
AATGAGTTCA AGTTGAGGGA CACATCCAGC CCAGGGTCCT TGCTGGCAAG CTAAAGAATG 5220
AGAGCCCTCT AACCCTCCCT GAAGTTTAGG GGAGACAGGA GAGCTGAGGA GATCCTTCTA 5280
GGGTGAAGGA GAGGTATCTG CTCTGACCAA CATGGCTAGG AGCAGAAGCA GTTGGACCAG 5340
TTACCCCTCA GAACCAGCCA TCCCCTCTTG GCTCTAAGGA GGCTGGGCCC CTTTCTGTTT 5400
AAGAATCTTA CTTTTCTTCA GAGAGAGGCA GCAAGCCTTT GTCCCCTCCC TGTTGGTCAA 5460
TAAACACCCC TGTGTGTAAC ATTAGTTTAT TTTACTGTCA GTTTGCTCCA GGACAGTCCA 5520
```

FIGURE 6C

```
TCTGGTAGAC CTCTGCTCCT AACTCACCAA GGTATGGCCC ACATTCCTCA CCCAGAAGAG 5580
TGCAGAAGAG AGCCTTAGAG AAAGGGTAAC AGTAACAAAG ATGGCCAGAA TAAAACAAAA 5640
ACTACTATCC TTTGTACCCA AATTGGTTTT GCTGAACCAG GAGGGGGTGT GTGAGTGTAT 5700
GTGTGTGTGT GTGTGTGTGT GTGTGTGTGT GTGTGTGTGT GTGTGTGTGT GTGTGTGTGT 5760
CTTGGGGGAC TTTTCATGCT AAAGAATATC TGATATTGGC GCCCATGCCA ACAGGGGTAT 5820
TGGGGAGAGT CAGGCTTCTG CAAACACAGT AAGCTGCCCA AGATGGATTG GTGGCCTGAA 5880
TCACCAAGGG GCAGGCTGAT CAGAGTGGAC AGAACATCAC AAGATAAGCC ACCCTGTGGG 5940
GCTCAGAAGA GGGAGTTTAC AAGAGGTAAA GGCCAAGCCA TTTATTATCC AAGACATGAC 6000
TCAAAATCAA AGTGCAAGGA GAGATTAGCT GGAGAGATGG GGCTGTCAGT GTGGGACACC 6060
TGACCTTGCA CTTATTAGTC ACTAGGCCAA GGAGCAGTCA CAGAGGGTGA CTGGGTCCTA 6120
CTCAGCTTGG AGCAGGCACG TGGAGAATGG GTGACCTCCA TCCTGATGGA GAGGGCTGAG 6180
CACCACCAGG TACAAGTGTT CCCTGTGTCT CATGCCAGGA TTCCTGGCCA GTTTTCAAAG 6240
GACTAAGGAC TCATCTCTGG TGGAAACAAA GTATCCAAGC CCTAAGCCCC ATTTTGGTCT 6300
AATTAAATCA GAACCCCTGG GGATGCAGGC TCTGAGCAGC AGGAGCTTTT TAAAAAGCTC 6360
CCAGGTGATT CTGATCAGCA GCTGGAACAA ACACAGCTAC AGGTTCAAAC AGAAAGAGGC 6420
AAAGCTAGGG AAAGCTTGGG ATGGGGAGCC TTCTTCCAGG CCAGTAGATG GAGGCTGGTT 6480
AGCAGTGGTG GCAGCTTCTC TCTGCCTGTC ATATAGCTAT CCATCCACTC ATCCATCCAT 6540
ACACCCACCC ATCCATTTAT GCACCCATCC TTCCATCCAT CCATCTATCC AGCTACCCAC 6600
CCACGCATCC ATCCAAACCT TCCTTTTCTC CTTCTTTCTT TCTTTTTTCC TTCACTCATT 6660
CATTTATCCA ACAGAGAACT GGTATTGTAC TAAATGTGGG AGATTTAATT AATTTTTAGA 6720
AGCTCTGTTG ATTGACTGAT TGTGCATGTA TGTGGACAGG TACATACCAC AGCACACGTG 6780
TGGCAATCGG AGAAAGGTTT TGGGTGTTGT TTTCTCTTCC CACCGTGTGG GTTCTGGGGA 6840
TTGAACTCAA ATTATCGGGC TGGTGGCAAG TGTCTTTACC ACCGAGCCAT TTGCTGACA 6900
CATCATTATT ATTAGAAAGC ATCTTATGTA GTCCAGGCTG GCCTCAAGCT TGCTATGTCG 6960
CCACGGATGA CCTTTAACTC CTGCTCTTCC AGCCTCCACC CGAGTGCTAG GTTTACAGGT 7020
GTTCAACTGG TGAATGCCTT TAATCCCAGC ACTCTGTGGG GGGGGGGGGG GAGGCGGATC 7080
CCTGAGTTGG AGGCCAGTTT GGTCTACAGA GTTTCAGGAT ACCTGGGGCT ATACAGGGAA 7140
ACCCTATCCC AAACAAACAA ACAAACAAAC AAAAAATATT CTGTGCAATA ATCACAGAGA 7200
TTAGAGGATA TTAGTAGGGT AGTAGGGCTG GTGAGGGAGA GTCATGCTTT CTTTTGTATT 7260
ATAATAGTAA AGTACTCACA AGATGCATTA TCTATCTATC TATCTATCTA TCTATCTATC 7320
TATCTATCTA TCTACCTACC TACCTACCTA TCCATCCATC CATCTATCGT ATAGCCCAGG 7380
CTGCTTTGAC TCTGAATGCT CCTATTTCTG GGTCAACTCT TCACCCCTAG TGTTGGGTTT 7440
```

FIGURE 6D

```
ACCAACACCC AGACATTTAT TTTATTTTGT TTTATTTTAT TAATCTAGGA GCTCAGGGTG 7500
GGACTCAGGG TCTTGTGCAT GCTAAGCAAG CTCTCTGCCA CAGAGCTGCA GCTCCAGTCC 7560
CCATTTGTT  CAGGTGACTC TGTGACAGTT GTCATATTCG CAGCGCTATG TAGCTCTCTC 7620
CACCTCCCAG TTCCAGCACT TTCTGGTCAT CCCAGTGGGC GGGCAACTCT GTGCTCACCA 7680
GTGCCCTGTT CCCTGTCTTC AGACCTACAT ATTTGCCTGT CTGAACAGTT CATGTAAATG 7740
GGATGCGTTC CTGTGTATTC TTTTATGGCT GGCCCCTTTA TCTTAGCACA GTTTGTGTTG 7800
GGCCATGTGT CACTGCTATA CTCTATCTTA TCATCATCTT ATGGCTTAAT AGTGTTCCTT 7860
TGTGTGGATA AACCACTTTC TGTTTCATTT ACTGATGGAA ATTTGTGGCC CCACCCCCAC 7920
CCTTTTTTTT TTTATTTGAG ACAAGGTCTT TCTGTGTAAT CTTGCAATCT TGGCTGTCCT 7980
GAGCTCACTC TGTAGACCAG GCTGTGAGGC TGTCCTTCCA CTTTTGACAC TCCTGTGAAC 8040
AGAGTAGCCA TGAACTTCAA AGACAATTTT CTGTTTTGGT TTGTTTTTTA CATTTGTGTG 8100
TGTATGCGTG TATATGTGCA TGTTTGTGTC TTCAGGTGCT CACATGTGTG TACCTGTGTG 8160
TGGGACAGAG AACAAACCGA TGTGCCATTC CTCAGATACT ACGCATCTTG TTAATATGTA 8220
TGTATTATGT ATGTTTATTT AGTGTGCCCA AGTATGCAGG TATTTTGTTG GAGTTTTCAC 8280
CTTCCCTTGT GGGCTCTCCG CATTAAACTC AGCTCCTCGG GCTAGTGAGC AATGCCTTCA 8340
CTCGATGAGC CATCTCGCTG CCCCTGCTGC CACCTCCTCC TTATTTCCCA GATGGGACTA 8400
CGCACTGCAC TGGCCTAAAG CTCACCAAGT CATCCAGAGT GGCTAGCCAG GGAGACTCAG 8460
GGATATGCTG GCCTCTGCCT CCACAGTGCT AGAATTACAG GCATACATCA CTGCTGGAAG 8520
ATTTTTAACC TGAATCCTGA GGATAGAGCA GGCACTCTAC CAATGGAGGG TTCTTTTTGT 8580
GTTTGGTTTG GTTTCCTCTG CATAAGATCA GGCAGTCTGA AATAGTGTAG CCTGGGCTAC 8640
ATAACATCTT GTCTCAAAAA GCCTATAGAG GTAGGGAGGT CGAGGCTAAA GAAGAGCCTT 8700
AAGCCGGCTG TGATAGCACA CAGGATAGCC TGCACTATAT AGCAAGACCT TGTTTCAAAA 8760
ACATGGAGGG AGGGGTATGT TTTAAGTGCT GGGCTGTGTA ACAGGCACTA AGGGAGCCAA 8820
TGTAGACATT TGACTAAGAA AGGATCATCA TCAAAGCCGG GTGGGCAGGG TAGAGGTTGG 8880
ACTACAGTGG TCAAGACCCC CATAGGAAGC CAGTTTCCCT TCTTCCTCTG GCCTCAAGC  8940
CTGGCTCGAC GGCCACTGCT CTCACATGCC TTCTCCTCTA GGCTCGTCCA CCATG       8995
                                                       exon 2
```

FIGURE 6E

REGULATORY SEQUENCES OF THE MOUSE VILLIN GENE—USE IN TRANSGENESIS

This is a continuation of International Application PCT/EP98/08009, with an international filing date of Dec. 9, 1998.

The invention relates to regulatory sequences of the mouse villin gene that efficiently drive transgenic expression in immature and differentiated epithelial cells of the intestine and uro-genital tracts.

Villin is a cytoskeletal protein which is mainly produced in epithelial cells that develop a brush-border responsible for absorption as in the digestive apparatus (epithelial cells of the large and small intestine) and in the urogenital tract (epithelial cells of the kidney proximal tubules). Because it is expressed in the proliferative stem cells of the intestinal crypts (16, 17), it is believed to be an early marker for commited intestinal cells. The multiple levels of relation control villin gene activity during mouse embryogenesis (18–20) and account for the strict pattern of tissue-specific expression observed in adults. Moreover, the expression of the villin gene in intestinal epithelial cells is conspicuously maintained in their correspondent carcinomas (21–24).

The specific expression pattern of villin suggests that it is an appropriate candidate for the characterization of regulatory sequences that could allow targeting of heterologous genes into a selected population of cells in the mouse digestive tract.

In order to design new constructs and systems enabling the targeted expression of genes in epithelial cells of intestinal or urogenital tracts, the inventors have investigated the underlying molecular mechanisms and particularly those responsible for the restricted tissue specificity of the expression of villin.

The invention therefore provides new regulatory sequences encompassing cis-acting elements involved in the regulation of the transcription and of the expression of the murine villin gene.

The invention also relates to recombinant constructs comprising said regulatory sequences, for the control of the targeted expression of determined nucleic acid sequences so-called (heterologous sequences or also transgenes), in cells or tissues originating from the intestinal mucosa.

A further object of the invention is to provide cells, tissues or organisms including animals, expressing said determined nucleic acid sequences in a targeted manner.

Transgenic mice are routinely used to study the molecular and cellular basis of normal and pathological states in intestinal mucosa (1–5). The major limitation regarding the targeting of exogenous transgenes in this tissue, is that the epithelium of the mouse intestinal mucosa is renewed every 2–5 days (6–8). The epithelial cells arise from multipotent stem cells functionally anchored at the base (more precisely in the lower third) of the epithelium's proliferative compartment, the crypts of Lieberkükn. These crypts display a monoclonal organization since they are each derived from a single progenitor cell (9). Descendants of stem cells multiply in the middle portion of each crypt (10), and gradually differentiate into four principal cell types. In the small intestine, absorptive enterocytes (constituting >80% of the epithelial cells), mucus-producing globlet cells and enteroendocrine cells migrate upward from the crypts to the apex of surrounding villi (whose colonic counterparts are hexagonal shaped cuffs) (11), where they become apoptotic and are exfoliated into the gut lumen (12). In contrast, antimicrobial peptides-secreting Paneth cells migrate to the bottom of the crypts, where they reside for about 20 days (13).

Given the remarkable protective effect of this epithelium, it is not unexpected that most previous studies aiming to induce neoplastic transformation in intestinal mucosa of transgenic mice have failed (14, 15). In these prior reports, the use of promoter sequences which direct oncogenes in non proliferating enterocytes located in the upper third of crypts produce only minor phenotypic abnormalities without tumorigenic consequences in the gut epithelium, suggesting that the residence time of these villus-associated cells may not be sufficient for the oncogenes to exert their effects. Furthermore this suggests that transgenic mouse models of neoplasia may require an efficient targeting of oncogenes in crypts stem cells or their immediate descendants. With this goal in mind, the human villin gene has been isolated and characterized (25). A 2 kb 5'-flanking region has been found to contain sufficient regulatory elements to promote tissue-specific expression of a reporter gene in intestinal and renal cell lines (26). In transgenic mice, this regulatory region is able to drive the expression of the human Ha-ras oncogene in the tissues in which the endogenous gene is actively transcribed. However low levels of expression were observed that did not trigger malignant tissue appearance into the gut of these animals.

The invention provides new means for the targeted expression of heterologous sequences in cells originating from intestinal and/or urogenital tracts. Advantageously, the invention encompasses but is nor limited to nucleotide sequences that should overcome at least in part, some of the deficiencies of the previously described gene constructs prepared with regulatory sequences of the human villin gene: especially having recourse to regulatory elements promoting the expression of the murine villin gene, the inventors have designed new DNA constructs that may improve the efficiency of the targeted expression of heterologous genes in transgenic animals, with respect to the results obtained when said heterologous genes are placed under the control of the human villin regulatory elements contained in the above disclosed 2 kb sequence.

The inventors have analysed an extended genomic region of the mouse villin gene with the goal of mapping elements localized at the 5' and/or 3' ends and possibly involved in promoting high levels of targeted expression of heterologous sequences in epithelial stem or differentiated cells, specifically originating from the intestinal mucosa.

As a result, the inventors have identified a transcriptional regulatory region that enables efficient targeted tissue-specific or cell-specific expression, reproducing the expression pattern of the endogenous villin gene in mice, including expression in the crypt stem cells of the colon and in differentiated cells.

In accordance with the invention the identified villin regulatory region provides a molecular tool for the establishment of new cell lines, including new immortalized cell lines, particularly epithelial cell lines originating from intestinal tissue. It also provides means appropriate for the preparation of transgenic organisms, especially transgenic animals, including transgenic mice, enabling the targeted expression of determined nucleotide sequences.

The invention therefore discloses appropriate tools for the study of pathological states related to a dysfunction of gene expression pattern or for the treatment or prevention of said pathological states, for example to enable targeted expression of a gene acting as repairer gene in order to compensate for the dysfunction of an endogenous gene, or to add a novel function in cells or to suppress a determined function or state, or its consequences.

The study of pathological states can benefit from the establishment of transgenic model animals wherein induction of a pathological state is obtained in relation with the targeted expression of genes. It also relates to the study of rescue of pathological states. The invention thus relates to a nucleotide sequence derived from the 5' sequence of the murine villin gene, having a size of 9 kb on an agarose gel, or a fragment thereof, comprising nucleotide elements having a cis-regulatory activity that promotes the transcription of the murine villin gene.

In accordance with the invention, the expression "nucleotide sequence" designates any of type of nucleotide sequence, especially DNA, whatever its origin, including genomic, cloned, amplified, recombinant or synthetic sequences.

The term "derived from" characterizes the fact that the sequence is defined with reference to the isolated endogenous sequence of the murine villin gene. Said nucleotide sequence derived from the murine villin gene nevertheless encompasses sequences obtained without having direct recourse to the native isolated gene. Furthermore, the structural and/or functional characterizing features of the nucleotide sequence may correspond to their native counterpart in the murine villin gene or may be modified as a result of mutation, deletion, truncation, or addition of nucleotides or nucleotide fragments provided its function of promoting the transcription and/or expression of the villin gene is not substantially affected.

The sizes of the nucleotide sequences which are indicated in the present patent application may vary: indeed, the indicated sizes correspond to the size deduced from the band visualized on an agarose gel, in conditions corresponding to those given in the examples.

Especially, a variation of the actual size of within the range of 20% to 5% especially around 15 or 10% of the sequence, is encompassed within the given size indication.

A nucleotide sequence of the invention is a sequence having a cis-regulatory activity that promotes the transcription of the murine villin gene thus enabling the transcription ending in the production of mRNA and subsequent expression of villin proteins, in intestine epithelial cells. Conditions appropriate to test said regulatory activity are described in the examples.

Where necessary, access to the genomic DNA of the murine villin gene is enabled through various available libraries. Clones obtained from a genomic library can indeed be used to isolate the nucleotide sequences of the invention, provided said clones contain sequences comprising a fragment having a size of at least 9 kb upstream from the translation initiation codon. Said fragment can be obtained from one clone or from overlapping genomic sequences contained in several clones. Probes derived from the cDNA of the villin gene can be used to identify appropriate clones in a genomic library of murine genes. Especially, such probes can be designed around the translation initiation codon and have advantageously at least 100 nucleotides, including sequences having 200 to 500 nucleotides, or more.

Such probes can also be designed starting from the sequence SEQ ID NO: 1 and can be synthesized or obtained by amplification. They can be derived from the 5' sequence upstream of the translation initiation codon.

Figure 2:
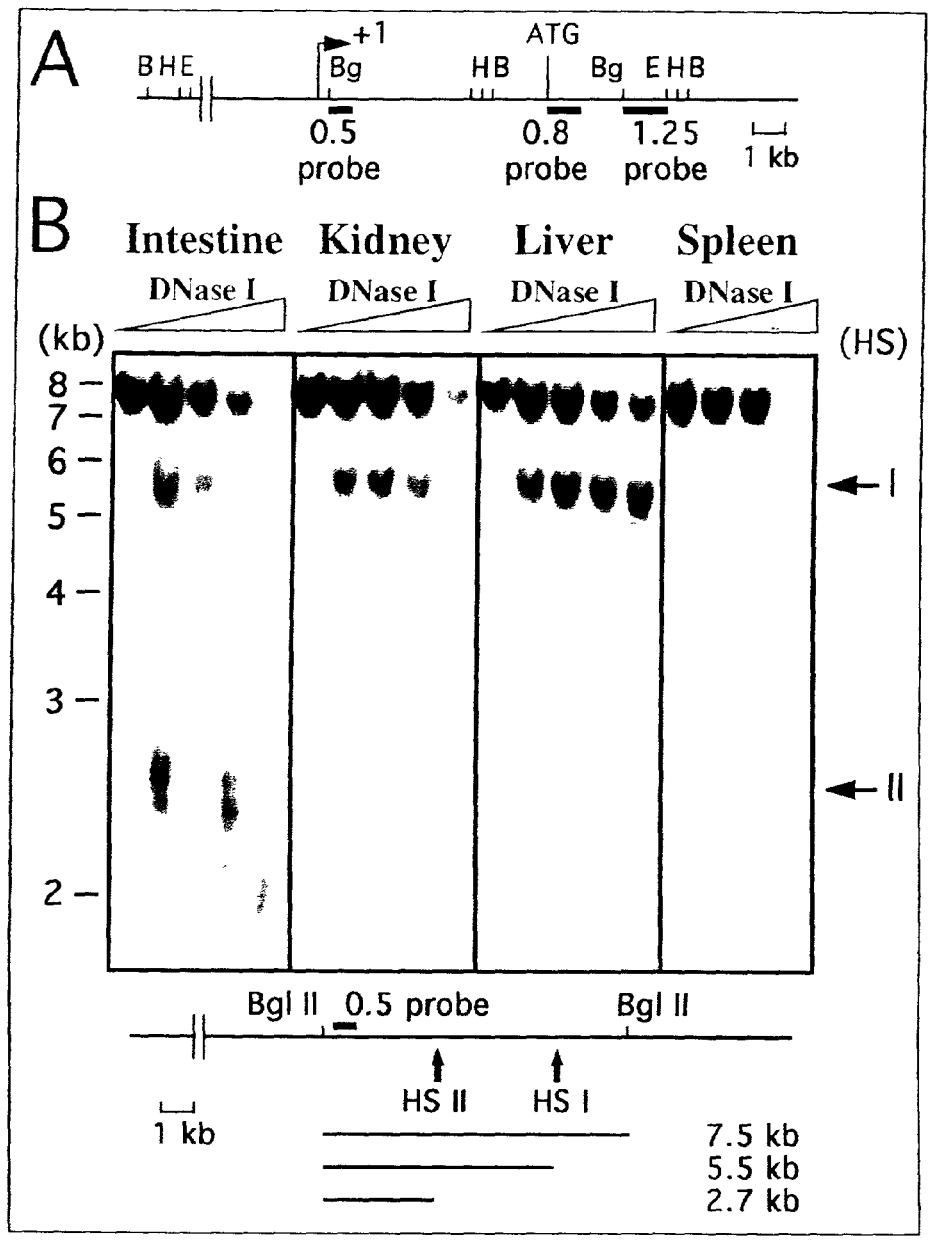
Figure 2:
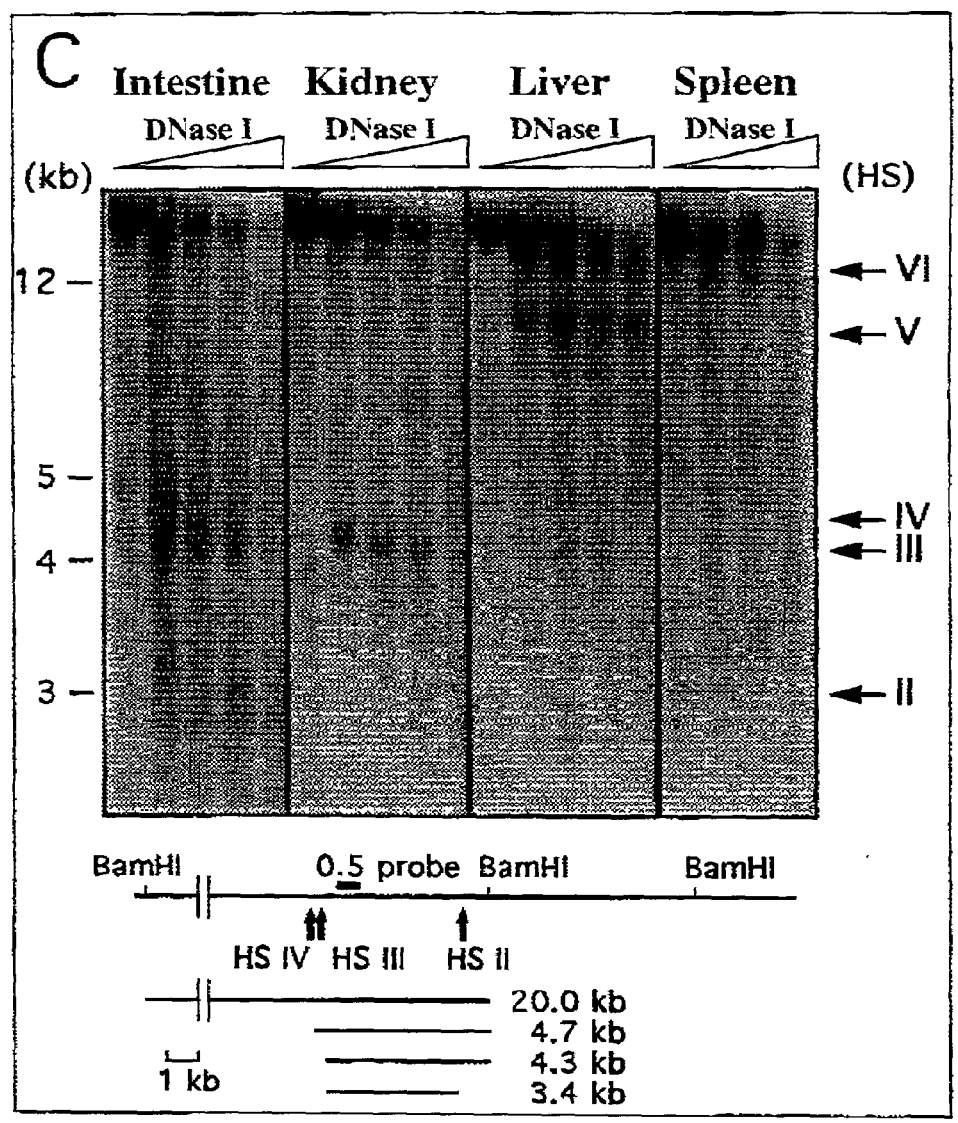

According to specific embodiments, the invention relates to various nucleotide sequences derived from said 9 kb sequence. Especially, the invention relates to:

- a nucleotide sequence which is the sequence extending 5.5 kb upstream and 3.5 kb downstream from the transcription initiation site of the murine villin gene;
- a nucleotide sequence which is identified as SEQ ID NO: 1 and which is represented on FIG. 6;
- a nucleotide sequence which comprises or which is the nucleotide fragment extending from the HS I to the HS IV Dnase I-hypersensitive sites;

The DNAseI hypersensitive sites can be mapped on a genomic DNA corresponding to the mouse villin gene with the probes described on FIG. 2.

- a sequence which comprises or which is the nucleotide fragment extending from the HS IV DnaseI-hypersensitive site to the translation initiation codon of the murine villin gene;
- a sequence which comprises or which is the nucleotide fragment extending from the nucleotide at around position −100 upstream from the transcription initiation site, to the translation initiation codon;
- a sequence which comprises or which is the nucleotide fragment extending 3.5 kb upstream from the transcription initiation site to the transcription initiation site and further comprises the translation initiation codon, and possibly the sequence of exon 1 and the sequence of exon 2 starting 5' from the ATG codon;
- a sequence which comprises or which is the nucleotide fragment extending from around the nucleotide at position −480 from the transcription initiation sequence, to the translation initiation codon;
- a sequence which comprises or which is the sequence extending 3.5 kb upstream from the transcription initiation site to the translation initiation codon, provided the region corresponding to intron 1, located between said sites is deleted, or deleted in part;
- a sequence which comprises or which is derived from the nucleotide sequence of the murine villin gene having a size of 9 kb on an agarose gel and extending 3.5 kb upstream from the transcription initiation site and 5.5 kb downstream from said site, or a fragment thereof, said nucleotide sequence or fragment thereof having a regulatory activity on the transcription of the murine villin gene and/or on the level of expression of the murine villin gene in intestine cells and/or in transgenic mice.

The transcription regulatory activity of the murine villin gene is cited as a reference for the identification of nucleotide sequences encompassed within the scope of the invention. The invention furthermore relates to a nucleotide sequence which is derived from said 9 kb sequence of the murine villin gene and which enables the transcription of a heterologous sequence, with respect to this gene.

According to another embodiment, the invention relates to a sequence having a regulatory activity on the transcription of a villin gene, which sequence is a non-human sequence and which hybridizes in stringent conditions with at least one of the above nucleotide sequences.

Especially variant nucleotide sequences can be obtained from other animals of the Vertebrates or Invertebrates groups, especially from mammals, or from birds especially chicken or from fishes. Referring to Invertebrates nucleotide sequences can be obtained from *Drosophila* or from *C. elegans*.

Although the above defined sequences have been shown as being able to promote efficient transcription and expression of heterologous sequences in epithelial cells of intestinal origin or in transgenic mice, their structural variations may affect the efficiency of their regulatory activity, either with respect to the tissue—or cell-specificity of this activity, or with respect to the expression level observed.

They can therefore be used to promote the targeted transcription and expression of genes (or more generally any nucleotide sequence of interest) in epithelial cells of the intestinal or uro-genital tracts, either in stem cells or in differentiated cells.

The invention thus relates to a recombinant nucleotide sequence which comprises a first nucleotide sequence and a second nucleotide sequence for which a tissue specific targeted expression in epithelial intestine cells is sought.

In a particular embodiment of the invention, the second nucleotide sequence is a sequence encoding a determined polypeptide, protein or peptide, all designated hereafter by the term "polypeptide".

The second nucleotide sequence may also be a sequence of therapeutic interest such as tumor suppressor gene, a functional inhibitor of a gene, an antisense sequence, an oncogene, an immortilizing gene, a normal gene for the restauration of a function, or more generally any sequence the targeted expression of which in epithelial cells of intestinal origin may present an interest, for instance in processes for preventing, controlling or curing pathological states including those states related to the development of tumors.

In a particular embodiment of the invention, the second nucleotide sequence codes for an antigen or an immunoglobulin or for fragments thereof, including variable chains or immunoglobulins.

In another embodiment of the invention, the second nucleotide sequence is an oncogene. A recombinant sequence of the invention comprising an oncogene may be used for studies relating to carcinogenesis especially in animal models expressing said recombinant sequence.

According to a specific embodiment of the invention the second nucleotide sequence which is placed under the control of the regulatory sequences of murine villin gene, is further placed under the control of an inducible system, for example the Tetracycline/Doxycycline mediated temporal control of gene expression in transgenic mice (Kistner A et al, 1996, PNAS, 93, 10933–10938).

The invention also concerns vectors containing the nucleotide sequences of the invention especially plasmids or cosmids, appropriate for the transfer and/or expression of these sequences in cells or transgenic animals.

The invention also concerns recombinant epithelial cells comprising a recombinant sequence as described above.

These epithelial cells encompass stem cells, especially crypt stem cells of the intestinal mucosa, or differenciated cells, especially committed intestinal cells.

The invention further relates to an epithelial cell originating from the kidney proximal tubules recombined with the nucleotide sequences of the invention.

The epithelial cells of the invention can be immortalized cells, especially as a result of the expression of an immortalizing gene (e.g., AgT (tsA58)) the expression of which is drived and targeted by the regulatory nucleotide sequence of the invention.

The administration of the recombinant nucleotide sequence of the invention may be made by the available techniques including ex vivo or in vivo administration processes, especially by electroporation, calcium phosphate precipitation, liposomes. . . .

The invention also concerns transgenic animals obtained by transgenesis of recombinant nucleotide sequences of the invention.

These transgenic animals encompass animals from the Vertebrates or Invertebrates groups and are especially birds for instance chicken or fishes or non-human mammals, more particularly mice. Invertebrates like *Drosophila* or Nematodes, like *C. elegans* can also be used for the preparation of transgenic animals expressing recombinant sequences of the invention under the control of regulatory sequences derived from their endogenous villin genes. Appropriate processes for the preparation of the transgenic animals expressing in a targeted issue specific way, recombinant nucleotide sequences, are disclosed in the following examples.

Such a process for the preparation of transgenic mice, advantageously comprises the steps of:
- administration of a transgenic into the pronuclei of fertilized eggs of mice,
- enabling the development of the recombined eggs to recover transgenic mice (founders) and verifying the presence of the transgene,
- if appropriate crossing the founders with non transgenic mice.

Further steps, including crossing between mice capable of expressing the sequences of the invention with mice expressing different sequences (e.g. sequences encoding inducible systems) in order to obtain double recombinant mice.

LEGENDS OF THE FIGURES

FIG. 1: Determination of the transcription start site of the mouse villin gene by primer extension. A, primer extension analysis was performed with mouse intestinal total RNA (30 µg) and with either the end-labeled villin oligonucleotide (generating a 105-nucleotides extension product) or the end-labeled mouse intestinal fatty acid binding protein gene (Fabpi) oligonucleotide used as a positive control (generating a 81-nucleotides extension product). The size of the fragments obtained by primer extension is shown at the left. The unrelated sequence ladder that was run in the same gel is used as a size marker. B, nucleotide sequence between the transcription start site (the bold adenosine designated as +1) and the initiation codon (the bold underlined ATG codon) of the mouse villin cDNA (SEQ ID NOs:11 and 12). Each of the splice junctions present in the intron 1 (indicated below) conforms to the consensus splice donor (the italique GT nucleotides) and acceptor (the italique AG nucleotides) patterns, described by Breathnach and Chambon (30). C, schematic respresentation of the organization of the 5'-flanking region of the murine villin gene. The open box represents the untranslated exon and the shadowed box represents the first coding exon. The size of the exon and the intron is indicated.

FIG. 2: DNase I-hypersensitivity in the mouse villin gene. A, a partial restriction map diagram of the mouse villin gene regions subcloned (−3.5 to +9.9 kb in respect to the transcription start site, indicated by an arrowhead). BamHI (B), BglII (Bg), Eco RI (E), Hind III (H) restriction sites, ATG initiation codon and the probes used to map the hypersensitives sites (0.5, 0.8 and 1.25 kb) are shown. B and C, intestine, kidney, liver and spleen nuclei were digested with increasing amounts of DNase I at 0° C. for 10 min (0, 20, 40, 80, 160 units). 10 µg of purified genomic DNA was digested with BglII (panel B), and BamHI (panel C), electrophoresed and transferred to a nylon membrane. Hypersensitives sites war revealed by probing with a $^{32}$P-labelled fragment of 0.5 kb. Positions of coelectrophoresed molecular weight markers are indicated at the left, and the hypersensitive bands are marked by arrows at the right. The maps represented below show the position of restriction sites, the deduced DNase I-hypersensitive sites (indicated by arrows) and the 0.5 kb probe used.

Figure 3:
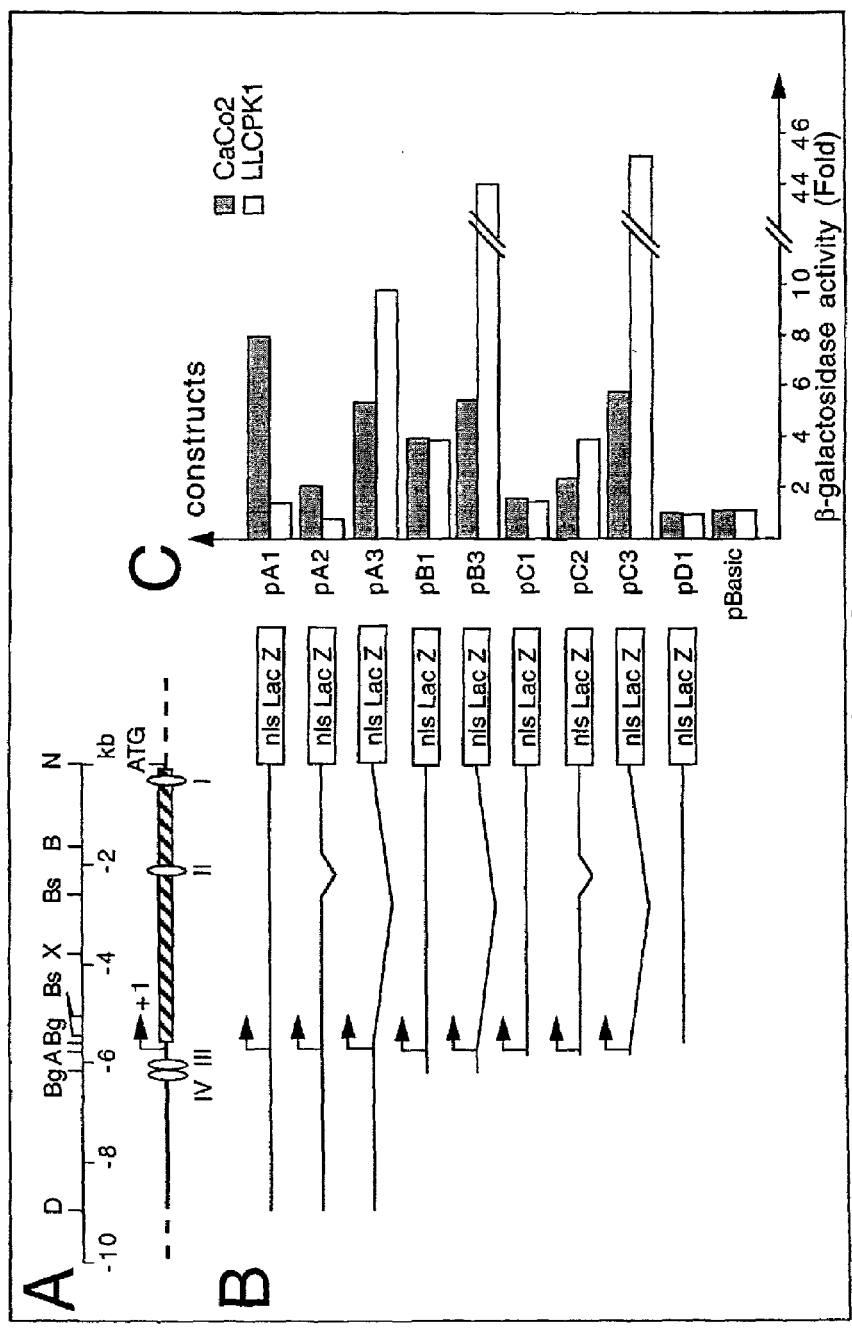

FIG. 3: Transient transfection analysis of the mouse villin promoter. A, above a partial restriction map diagram of the mouse villin gene from 9 kb with respect to the translation initiation codon. ApaI (A), BamHI (I), BglII (Bg), BstEII (s), DrdI (D), NcoI (N) and XbaI (X) restriction sites are shown. The schematic representation below shows the location of the four hypersensitive sites (I–IV) as well as the 5.5 kb intron (represented by a cross-hatched rectangle) separating the transcription start site (indicated by an arrowhead) and the translation initiation codon. B, diagrams of the various constructs generated by deletion. Different portions of the 5'-flanking region of the mouse villin gene were used with the E. coli β-galactosidase gene containing the nuclear localization signal (nls). C, β-galactosidase activities resulting from transient transfections into CaCo2 colon cells (shadowed bars) or LLCPK1 kidney cells (open bars) with the reporter constructs generated (represented in panel B). Basal activity resulting from the promoterless pBasic plasmid was set arbitarily at 1. Values indicate the average of at least three independent transfections.

Figure 4:
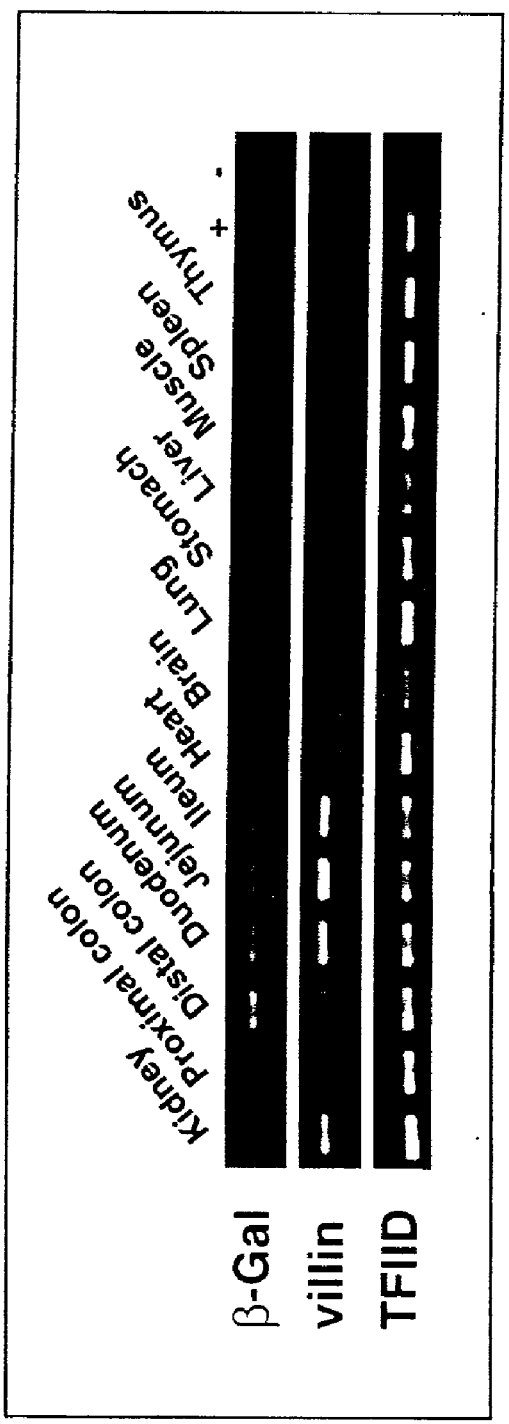

FIG. 4: Expression pattern of the transgene. Transgene (β-Gal) specific-transcripts were detected by reverse transcription-PRC in a ethidium bromide containing agarose gel. Above each lane, the different tissues tested and the controls, (+): kidney mRNA from a mouse in which the β-galactosidase was inserted at the villin locus (32), and (−): distilled $H_2O$ as a template RT-PCR were also performed on mRNAs of the endogenous villin gene and the ubiquitous TFIID gene.

Figure 5:
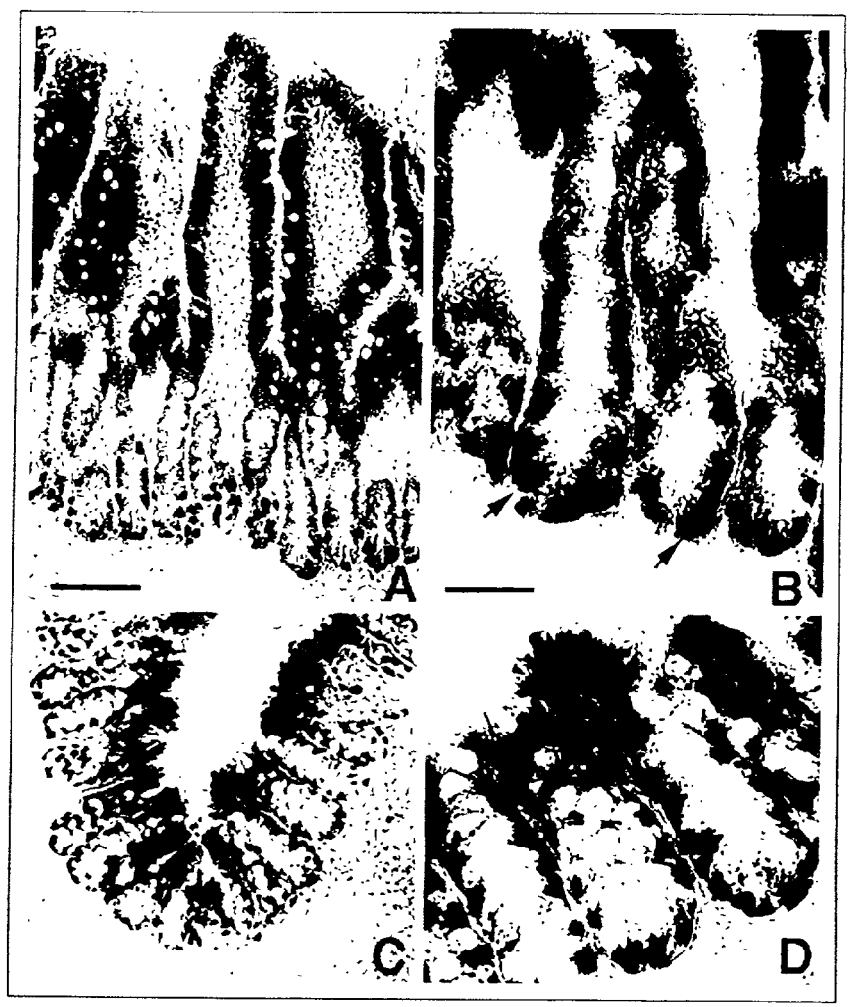

FIG. 5: β-galactosidase activity in sections of small intestine and colon from transgenic mice. Tissues were removed from transgenic mice, fixed, and stained for β-galactosidase activity with X-Gal as described β-galactosidase activity was observed in the epithelial cells, both immature and differentiated, along the crypt-villus axis in the small intestine (panel A). Note that the differentiated cells exhibited a strong signal as did the villus-associated cells and the Paneth cells (arrows) localized to the bottom of the crypt (panel B). The epithelial cells of the colon were also stained (panel C), particularly all the cells in the crypt (panel D). Bars, 100 μm (panels A and C), 40 μm (panels B and D).

FIG. 6(A–E): Sequence of the genomic DNA of the murine villin gene (SEQ ID NO:1) comprising cis-acting elements capable to promote the transcription of the murine villin gene in intestinal mucosa and kidney proximal tubules. The sequence comprises the transcription initiation site at position 3442 followed by the sequence of exon 1 containing 46 pb, the translation initiation codon at position 8993, the sequence of intron 1 extending from nucleotide 3488 to nucleotide 8981.

Figure 7:
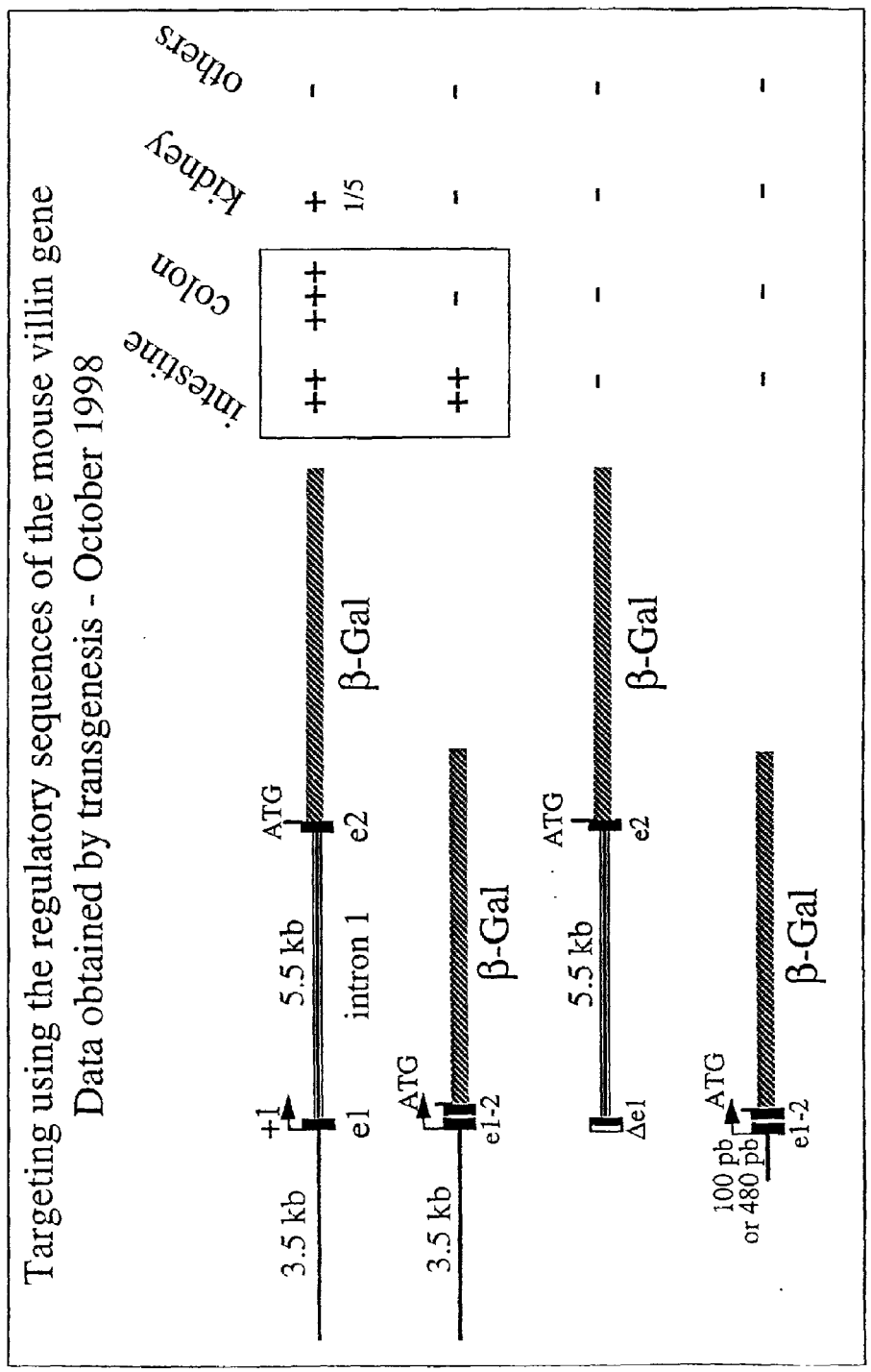

FIG. 7: Targeted expression of the β-galactosidase protein using regulatory sequences of the mouse villin gene. The data have been obtained by transgenesis.

Figure 8A:
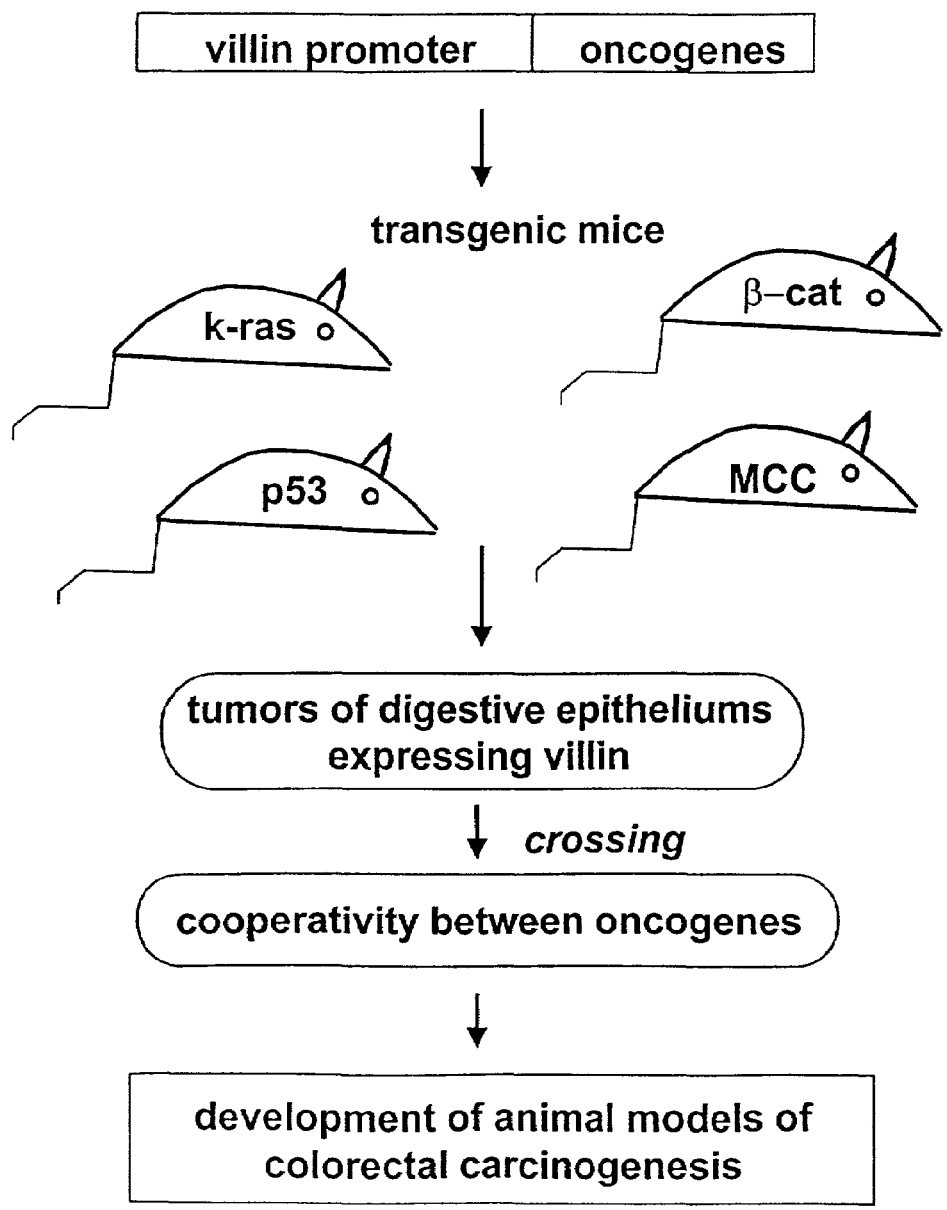
Figure 8B:
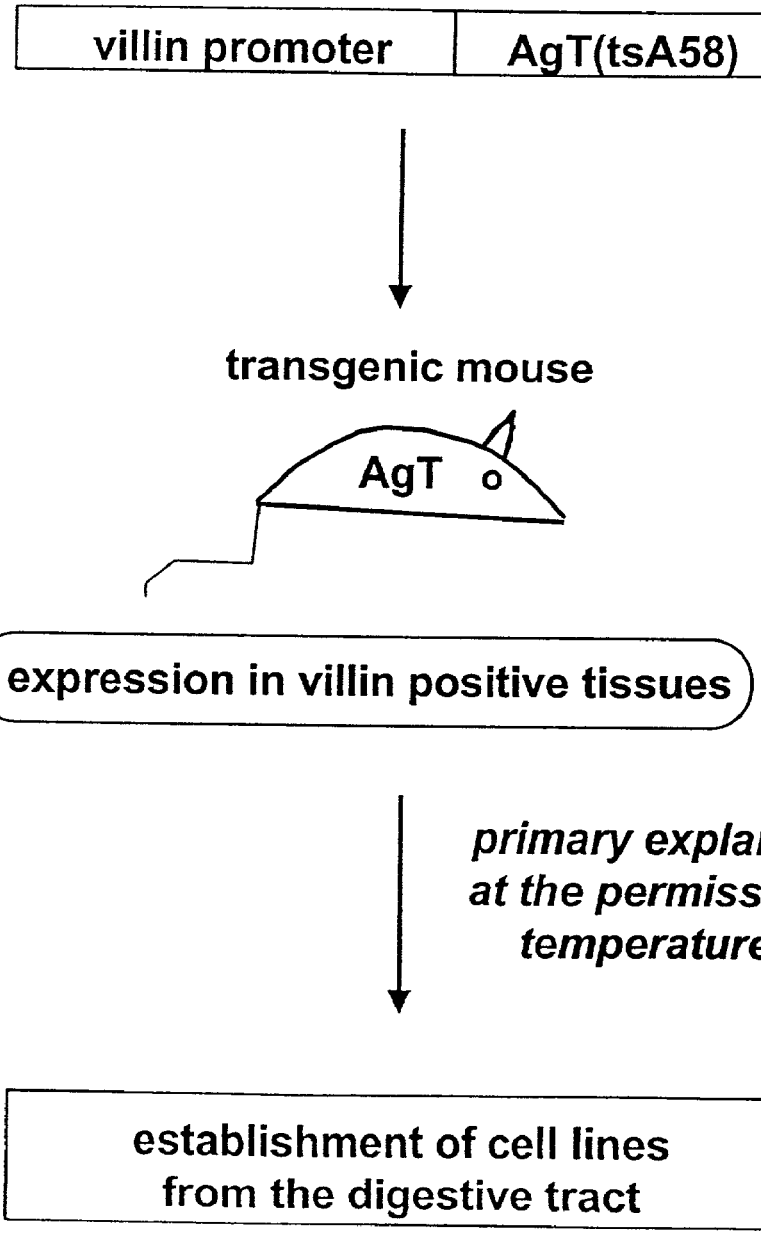
Figure 8C:
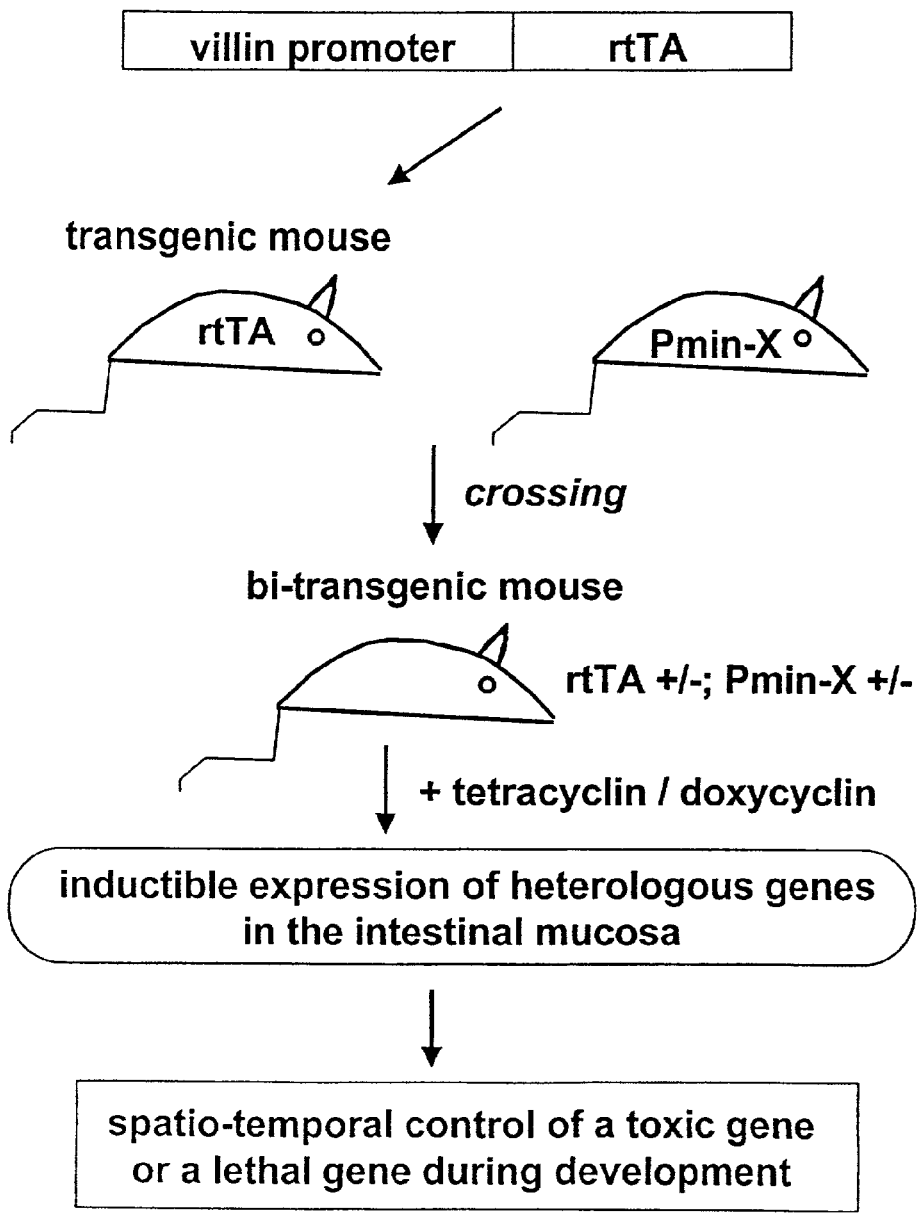
Figure 9:
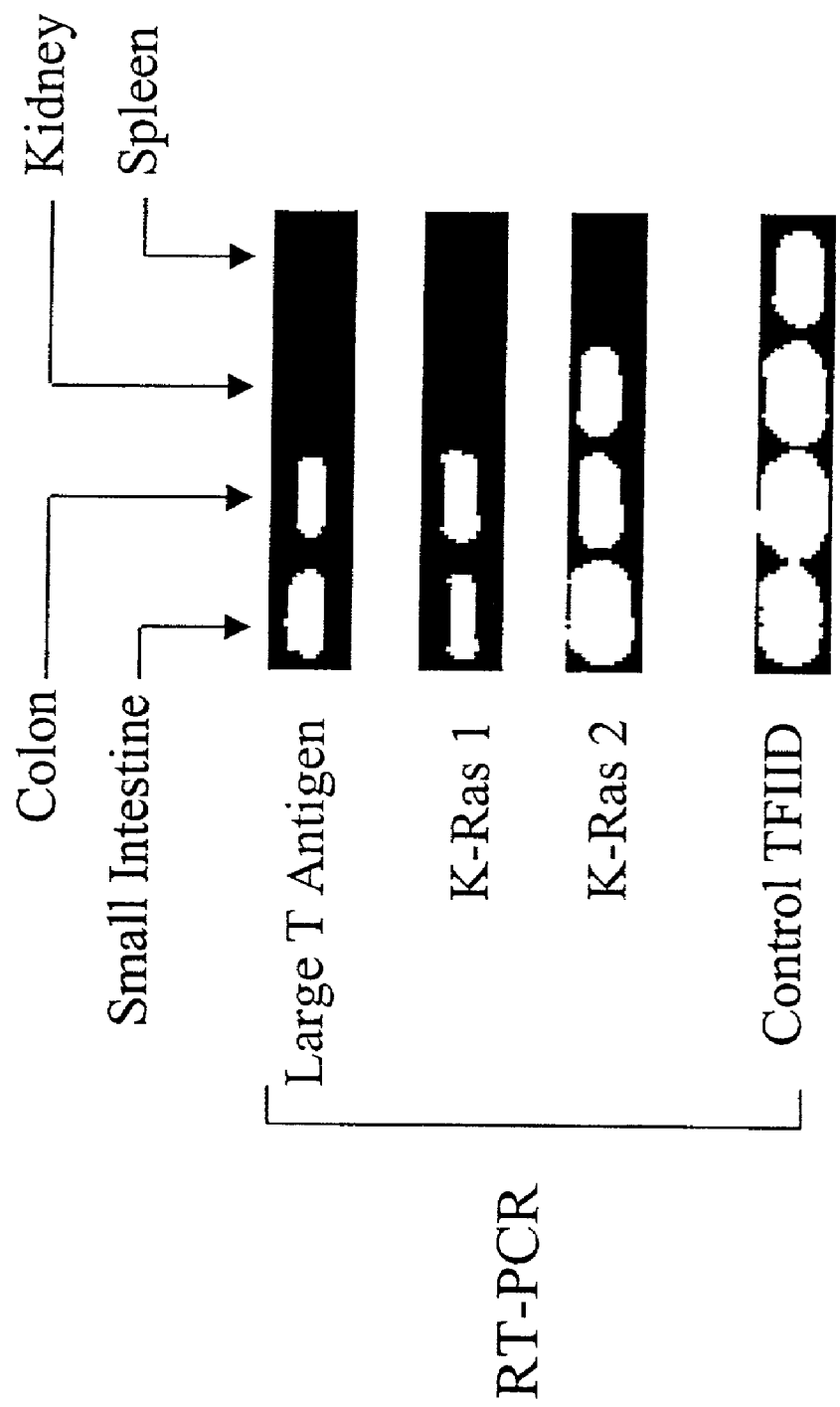

FIG. 8(A–C): Protocols for the preparation of transgenic mice expressing determined nucleotide sequences under the control of the murine villin gene regulatory sequences.

EXPERIMENTAL PROCEDURES

A large genomic region of the mouse villin gene has been analyzed. A 9 kb regulatory region of the mouse villin gene (harbouring 3.5 kb upstream the transcription stan site and 5.5 kb of the first intron) was able to promote transcription of the Lac Z reporter gene in small and large intestines of transgenic mice a transmissible manner, and thus efficiently directed subsequent β-galactosidase expression in epithelial cells along the entire crypt-villus axis. In the kidney, the transgene was also expressed in the epithelial cell of the proximal tubules but is likely sensitive to the site of integration. A construct lacking the first intron restricted β-galactosidase expression to the small intestine. Thus, the 9 kb genomic region contains the necessary cis-acting elements to recapitulate the tissue-specific expression pattern of the endogenous villin gene. Hence, these regulatory sequences can be used to target heterologous genes in immature and differentiated epithelial cells of the small and/or large intestinal mucosa.

Here we report the analysis of tissue-specific expression of the mouse villin gene using: (i) DNase I-hypersensitive sites assays, (ii) transient-transfection assays and (iii) transgenic mice.

Cell Culture and Ex Vivo Transient Transfection.

Human colon carcinoma CaCo2 cells were cultured at 37° C., 10% in CO2, in Dulbecco modified Eagle medium supplemented with 10% fetal serum, 1× nonessential aminoacids and 5 mM L-glutamine. Pig Kidney proximal tubules derived-LLCPK1 cells and canine kidney distal tubules derived-MDCK cells were cultured at 37° C., 10% CO2, in Dulbecco modified Eagle medium supplemented with 10% fetal calf serum and 5 mM L-glutamine. Cells cultures, approximately 50% confluent in 60 mm-dishes containing serum-free medium, are cotransfected using 15 μl of Lipofectin reagent (Life Technologies, Inc.) with 5 μg of each β-galactosidase reporter plasmid construct and 5 μg of the control plasmid, pRSVLuc, which contains the luciferase gene under the control of the Rous sarcoma virus promoter. The serum-free medium was changed to growth culture medium 6 h after transfection, and cells were harvested 48 h later. Cell extracts were assayed by chemiluminescent detection of both β-galactosidase (Galacto-Light, Tropix, Inc.) and luciferase (Luciferase Assay Kit, Tropix, Inc.) activities using a luminometer (Bertold). β-galactosidase activity (light units) was corrected for variations in transfection efficiencies as determined by luciferase activity. The volume of cell extracts used in the β-galactosidase and luciferase assays are adjusted such that the enzyme activity was always within the linear range of the assay. All transfections were repeated at least three times. Results are expressed as -fold induction over that of the vector without promoter, pBasic.

Primer Extension Analysis.

Total RNA was isolated from mouse intestine with RNA NOW reagent (Biogentex) under the conditions suggested by the supplier. For primer extension assay, 2 ng of $^{32}$P-labeled oligonucleotide probe (5'-GAGTGGTGATGT-TGAGAGAGCCT-3'; SEQ ID NO:2) complementary to nucleotides +81 to +103 of the murine villin cDNA (GenBank Accession No. M98454) was hybridized with 30 μg of total RNA at 60° C. (0.25 M KCl, 10 mM Tris-HCl, pH 7.5, 1 mM EDTA) for 90 min. Transcription with 5 U/μl of Moloney murine leukemia virus reverse transcriptase (Life Technologies, Inc.) was carried out at 37° C. for 90 min in a 300 μl of a solution containing 75 mM KCl, 3 mM $MgCl_2$, 50 mM Tris-HCl (pH 8.3), 10 mM dithiothreitol, 0.75 mM deoxynucleoside triphosophates, 75 μg/ml actinomycin D and 0.3 U/μl RNasin. The primer extension products were separated by electrophoresis in denaturing 8% polyacrylamide gels. The full-length extension product (105 nucleotides) was obtained by comparison with the length of the comigrating sequencing reaction products. A primer extension control experiment was performed on the same total RNA preparation, using a $^{32}$P-labeled oligonucleotide probe (5'-CATAGTTCTCGTTCCGGT-3'; SEQ ID NO:3) complementary to nucleotides +63 to +80 of the mouse intestinal fatty acid binding protein (I-FABP) cDNA and generating a 81-nucleotide extension product (27).

DNase I-Hypersensitive Sites Analysis.

Tissues from 30 mice were used per assay of intestine, kidney, liver and spleen. Nuclei preparation and DNase I digestion were performed as described (28) with minor modifications. Nuclei were digested without or with 20 to 160 units of DNase I (DPRF Worthington) for 10 min at 0° C. Genomic DNA was purified by three rounds of (1:1) phenol-chloroform extraction followed by chloroform extraction and precipitation with ethanol. 10 μg of each sample was digested overnight with restriction enzyme (BamHI or BglII). The DNA fragments were separated by electrophoresis on a 0.8% agarose gel in TAE (40 mM Tris (pH 7.2), 20 mM sodium acetate, 1 mM EDTA), transferred onto a charged nylon membrane (Hybond-N$^+$, Amersham), and hybridized at 65° C. overnight with a random-primed (rediprime, Amersham) $^{32}$P-labeled probe. The probe, the BglII-PstI probe (0.5 kb) (as indicated in FIG. 2) was used to map the DNase I-hypersensitive sites in the BamHI, BglII fragments. The filter was washed using (1×SSC (0.15 M NaCl, 15 mM sodium citrate, pH 7.0), 0.1% SDS, 55° C.) and exposed to film overnight at −70° C. with an intensifying screen.

Plasmids Construction.

All constructs described were subcloned into the pBluescript II KS vector (Stratagene) with fragments isolated from a λDASHIL phage containing a 16.3 kb region (9 kb upstream and 7.3 kb downstream from the translation initiation codon) of the mouse villin gene (29). The pD1 construct (as described in the FIG. 3B) was prepared by ligating a BamHI fragment of 5.1 kb (1.8 kb upstream from the ATG translation initiation codon of the mouse villin gene, subcloned 5' to the nuclear localization signal-β-galactosidase gene-SV40 polyadenylation site, using a polymerase chain reaction (PCR) strategy) at the BamHI site in a plasmid containing the 3.7 kb region of the mouse villin gene (immediately 5' to the 1.8 kb region described above). The pA1 and pA2 (containing an internal 1 kb deletion) constructs have resulted from several steps based on the BstEII sites present in the 3.7 kb region described above and in a plasmid containing the 3.5 kb region of the mouse villin gene (immediately 5' to the 3.7 kb region). The pC1 and pC2 constructs were derived from the pA1 and pA2 plasmids cut with ApaI and re-ligated, respectively. To generate the pB1 construct, a BglII fragment (480 bp) from the 3.5 kb region described above was excised and cloned into the KpnI site of the pC1 plasmid. The pA3, pB3 and pC3 constructs correspond to the pA1, pB1 and pC1 deleted from the intron 1 (FIG. 3B). The sequence between the transcription initiation start site and the translation initiation codon, excluding the intron 1, was deduced from that of the murine villin cDNA (GenBank Accession No. M98454) and was introduced into the BglII-NcoI sites of the pC1 construct by using a dimerized oligodimer made of a coding-strand oligonucleotide (5'-GATCTCCCAGGTGG TGGCTGCCTCTTCCA-GACAGGCT CGTCCAC-3'; SEQ ID NO:4) and a non coding-strand oligonucleotide (5'-CATGGTGGAC-GAGCCT GTCTGGAAGAGGCAGCCACCAC-CTGGGA-3'; SEQ ID NO:5), resulting in the pB3 construct. The pA3 and the pC3 constructs were derived from the pB3 plasmid by ligating an ApaI fragment (3.1 kb) and a BglII fragment (480 bp) from the 3.5 kb region described above, at the ApaI site in the pB3 plasmid respectively. Subcloning steps were confirmed by DNA sequencing.

Transgenic Mice Generation.

The transgenes digested with XhoI-NotI, purified by gel elution and Elutip Columns (Schleiche & Schuell). The linear fragments were supended in 10 mM Tris-HCl, pH 7.4, 0.2 mM EDTA and were injected into the pronuclei of the fertilized eggs of the B6/D2 mice. Mice cog transgenes (founders) were first identified by PCR of genomic DNA isolated from a short segment of tail to confirm the presence of the β-galactosidase gene and then analyzed by Southern blotting to determine the copy number of the integrated transgene. Each founder animal harbored one copy of the transgene per genome. Small intestine, colon, kidney, stomach, liver, heart, lung, thymus, brain, spleen and muscle were dissected from transgenic mice, cut in small pieces, quickly frozen in liquid nitrogen-cooled isopentane either prepared for total RNA extraction or embedded in Tissue-Tek O.C.T Compound (Sakura Finetek) blocks to perform cryosections.

Reverse Transcription-PCR Analysis.

Total RNA was isolated from mouse tissues described above, with SV Total RNA Isolation System (Promega) under the conditions suggested by the supplier. 20 ng of pd(N)$_6$ random primer (Pharmacia) were hybridized with 2 μg of total RNA at 70° C. for 10 min in distilled water. Reverse transcription with 200 U of Moloney murine leukemia virus reverse transcriptase (SuperScript II, Life Technologies, Inc.) was carried out at 37° C. for 90 mm in a 20 μl solution of 1× First Strand Buffer (Life Technologies, Inc), 10 mM dithiothreitol, 0.5 mM deoxynucleoside triphosphates and 0.4 U/μl RNasin. 2 μl of the resulting cDNAs, were amplified by PCR reaction in 50 μl for 40 cycles. Each cycle consisted of 60 set at 94° C., 60 sec at 51° C. (for transgene and villin) and 57° C. (for TFIID), and 30 sec at 72° C. For the transgene primers, 5'-CAACTTCCTAA-GATCTCC-3' (SEQ ID NO:6) coding strand and 5'-AT-TCAGGCTGCGCAACTGTT-3' (SEQ ID NO:7) non-coding strand were used, generating a 250 bp product. For villin amplification 5'-CAACTTCCTAAGATCTCC-3' (SEQ ID NO:6) coding strand primer and 5'-GCAACAGTCGCTG-GACATCACAGG-3' (SEQ ID NO:8) non-coding strand primers were used, generating a 473 bp product; for TFIID amplification 5'-CCACGGACAACTGCGTTGAT-3' (SEQ ID NO:9) coding strand primer and 5'-GGCTCATAGC-TACTGAACTG-3' (SEQ ID NO:10) non-coding strand primer were used, generating a 220 bp product. In all cases, one-fifth of the PCR product was run on an ethidium bromide containing agarose gel.

Detection of β-Galactosidase Activity.

Cryosections (5 μm) from the tissues described above are then dried overnight at room temperature, fixed with 3% paraformaldehyde for 5 min, washed in phosphate buffered saline and incubated in a staining solution that contained 0.4 mg of 5-bromo-4-chloro-3-indolyl-β-D-galactopyranosid (X-Gal) per ml, 4 mM potassium ferricyanide, 4 mM potassium ferricyanide, 2 mM MgCl$_2$ at 37° C. for 8 h. After staining, the sections were again washed in phosphate buffered saline, mounted and examined histologically to detect the expression of exogenous β-galactosidase.

RESULTS

Determination of the Transcription Start Site.

To determine the transcriptional start site of the mouse villin genes total RNA was isolated from intestine and analysed by primer extension assay using an oligonucleotide complementary to the mouse villin cDNA downstream of the ATG translational start site. The efficiency of the reaction was confirmed by primer extension of the mouse intestinal fatty acid binding protein (I-FABP) gene (fabpi) from the same RNA preparation (27). Analysis of the fabpi extension product on a sequencing gel by comparison with a sequence ladder (FIG. 1A) revealed a strong signal band of a size of 81 bp as expected. The extension product of villin was 105 pb indicating that the transcriptional start site (an adenosine residue subsequently designed as nucleotide +1) was 57 nucleotides upstream of the translation initiation codon of the murine villin cDNA (FIG. 1B). Comparison of the genomic sequence encompassing 9 kb upstream from the ATG initiation codon with the cDNA sequence, position of splice site consensus sequences in the 9 kb genomic sequence (FIG. 1B) and determination of the transcription start site reveal that the mouse villin gene has one transcription start site which is separated from the ATG initiation codon by a 5.5 kb intronic region (FIG. 1C).

DNase I-Hypersensitive Sites in the Mouse Villin Gene.

To characterize the key regulatory regions involved in the specific control of villin expression, we have mapped the DNase I-hypersensitive sites (31) in the mouse villin gene (along a region extending 9 kb upstream and 4.4 kb downstream from the translation initiation codon, as represented in FIG. 2A). The chromatin form of the mouse villin gene in different tissues (intestine, kidney, liver and spleen) was submitted to limited DNase I digestion and subsequently digested with the appropriate restriction enzymes. Accordingly, nuclei were isolated from intestine, kidney, liver and spleen. The Dnase I-digested DNA was restricted by BlgII and hybridized with a 0.5 kb probe homologous to the 5' of the 7.5 kb BlgII fragment (FIG. 2B). Two sets of Dnase I incubation-related fragments were detected, migrating at 5,5 and 2,7 kb, and corresponding to hypersensitive sites designated as HS I (located at approximately +5.5 kb downstream from the transcription start (+1) site, just upstream the ATG initiation codon) and HS II (located at approximately +3 kb downstream from the (+1) site, respectively. HS I was observed in nuclei isolated from intestine, kidney and liver, whereas HS II was only present in intestinal tissue. No specific hypersensitive sites were detected in nucleic isolated from spleen. The presence and location of these hypersensitives sites were detected in nuclei isolated from spleen. The presence and location of these hypersensitives bands were confirmed by stripping and rehybridizing the same blot with the 0.8 kb probe (FIG. 2A) homologous to the other end of the 7.5 kb BglII fragment (data not shown). Using BamHI digestion and the 0.5 kb probe (FIG. 2C), five sets of DNase I-treated nuclei-related fragments were detected, migrating at 3.4, 4.3, 4.7 and approximately 10 and 15 kb, corresponding to the hypersensitive sites HS II (previously identified and consequently confirmed), HS III (located at approximately −0.5 kb upstream from the (+1) site), HS IV (located at approximately −1 kb upstream the (+1) site), HS V (located at approximately −10 kb upstream from the (+1) site) and HS VI (located at approximately −15 kb upstream from the (+1) site), respectively HS III was observed in nuclei isolated from both intestine and kidney, whereas HS IV was only present in) intestinal tissue as HS II. The hypersensitive site HS V and HS VI were only present in liver tissue (in which villin is weakly expressed) and were located far upstream from the transcription start site in regions (i) which have not been subcloned and (ii) which could belong to an adjacent gene; for these reasons, these hepatic-specific hypersensitives sites were not analyzed further. As for BglII digestion, no specific hypersensitive sites were detected in nuclei isolated from spleen. Using other independent restriction digestions (EcoRI and HindIII) and the 0.5, 0.8 and 1.25 kb probes (FIG. 2A) to map the locations of the hypersensitive sites, similar results were obtained (data not shown)

In conclusion, four major distinct DNase I-hypersensitive sites (HS I to HS VI) were shown to be present in the region extending from −1 kb to +5.5 kb in respect to the transcription start site (FIG. 3A) of the mouse villin gene. These sites were detected in intestine (HS I to HS IV), kidney (HS I and HS III) and liver (HS I), tissues in which villin is expressed, but they were not found in spleen, a tissue that does not produce villin. These findings correlate with the tissue-specific control of villin gene expression, and suggest that the putative critical regulatory elements lie within these regions. HS II and HS IV were only detected in intestine and are probably associated with tissue-specific transcription factors binding sites involved in the positive control of villin gene intestinal expression.

Analysis of Promoter Activity by Transient Expression.

To test the effects of the segments containing the DNase I-hypersensitives sites (FIG. 3A) on transcriptional activity and to define more precisely the element(s) controlling villin gene expression in the intestine, segments were subcloned upstream of a promoterless Lac Z plasmid (coding for the bacterial β-galactosidase gene with a nuclear localization signal sequence) (FIG. 3B). The resulting recombinant plasmids were tested by transient transfection assays in cultures cell lines. The construct pA1 contained all the subcloned regions downstream from the ATG initiation codon, encompassing the four DNase I-hypersensitive sites (HS I to HS IV) described above and the 5.5 kb intronic sequence, intron 1. Plasmids pA2 and pA3 were identical to pA1 except for the presence of intestine-specific hypersensitive site HS II and intron 1, respectively. Plasmid pB1 and plasmid pC1 were similar to plasmid pA1, but lacked the regions extending from −480 bp to −3.5 kb and −100 bp to −3.5 kb according to the transcription start site, respectively. Plasmid pC2 was identical to pA2, but lacked the region extending from −100 bp to −3.5 kb. Plasmids pB3 and pC3 were identical to pB1 and pC1 except for the presence of intron 1, respectively. The plasmid pD1 was identical to pA1 except for the presence of the transcription start site and the region extending upstream from this site. The plasmid pBasic, which does not contain a promoter or enhancer, and a pControl plasmid which possesses the SV40 promoter, were also tested in each experiment. Transient transfections were performed in the human colon enterocytes-like CaCo2 cell line and the pig kidney proximal tubules-derived LLCPK1 cell line which express villin, and in kidney epithelial cells in which no villin expression is detected, MDCK (a canine kidney distal tubules-derived cell line). Transcription from the villin promoter was measured by assaying β-galactosidase activity in extracts made from the transfected cells, and the results were expressed as -fold induction over that of the promoterless vector, pBasic (FIG. 3C). High levels of β-galactosidase activity in the pControl transfected cell lines (CaCo2 cells, 50-fold over that of pBasic; LLCPK1 cells, 98-fold) demonstrated the presence of efficient general transcription/translation machineries in these cells. Very low levels of β-galactosidase activity in pD1 both transfected cells compared to pBasic transfected cells showed that the transcription stan site was necessary for an efficient specific transcription of the reporter gene and that nonspecific transcription was not initiated elsewhere in the villin regulatory sequences. The construct pA1 expressed the β-galactosidase gene at the highest level in CaCo2 cells (8-fold over pBasic) as compared with LLCPK1 cells (1.5-fold over pBasic) suggesting that the four DNase I-hypersensitives sites together with the first intron are necessary to promote efficiently transcription in cells of intestinal origin. Deletion of the fragment containing the intestinal-specific hypersensitive site HS II (pA2) dramatically decreased β-galactosidase expression in CaCo2 cells (2-fold over pBasic) to about 25% of that of pA1, demonstrating that a major element which confers intestinal activity was confined wit this fragment. Similar results were obtained when the region upstream from the transcription start site (encompassing HS III and HS IV) was almost wholly deleted with or without HS II (pC1 and pC2, respectively). The deletion of the intronic region alone (pA3), or in combination with deleted sequences upstream from the transcription start site (pB3 and pC3 extends only from −480 and −100 bp, respectively), affected to a lesser extent β-galactosidase expression in the same intestinal cells (5.5-fold over pBasic), with a decrease to only about 65% of that of pA1, demonstrating that the regulatory elements which lay within 100 bp were sufficient to promote transcription in cultured cells. However the level of β-galactosidase activity increased strongly when the plasmids pA3, pB3 and pC3 were transfected in LLCPK1 cells (10, 44, and 45-fold over pBasic, respectively) showing that the absence of the first intron, in combination with the lack of intestine specific HS IV, was able to promote transcription in a kidney cell line. This would suggest that negative elements which confer repression in kidney transcription are confined in these elements.

To test specificity, the villin promoter-related constructs were transfected in MDCK cells, which do not express villin. After transfection, these cells showed only base-line levels of β-galactosidase activity when compared to pBasic-related activity (data not shown), demonstrating that the villin regulatory sequences were unable to promote efficient transcription in non expressing villin cells, and that consequently the expression of the reporter gene in CaCo2 and LLCPK1 cells is specifically dependent upon these regulatory sequences. Taken together, these results from transient transfection of cultured cells demonstrate that (i) the mouse villin genomic sequence, extending from −3.5 to +5.5 kb, directs specifically an efficient level expression of the β-galactosidase reporter gene in intestine-derived cells, (ii) this level is dramatically reduced when the intronic intestine-specific hypersensitive site HS II or the region upstream from the (+1) site is deleted, (iii) lack of the entire first intron seems to partially restore the intestine-related ability in promoting transcription, and (iv) lack of the entire first intron in combination with intestine specific hypersensitive site HS IV is correlated with a strong increase of ability in promoting transcription in kidney-derived cells.

Analysis of Transgenes Expression in Mice:

Since the −3.5 to +5.5 kb region of the mouse villin contained the enterocytes-like-specific promoter/enhancer activity in transient-transfection assays, we examined the ability of this region to drive intestine-specific expression of the β-galactosidase reporter gene in transgenic mice. The construct pA1 was then prepare, after excision of the plasmid sequence, and injected into fertilized eggs. Five founder animals which contained the pA1 construct as a transgene Were obtained. The founder mice were analysed for mRNA reporter gene expression in several adult tissues by reverse-transcription PCR (RT-PCR) analysis. From the same cDNA samples, products encoding β-galactosidase, villin and TFIID were analyzed. The PCR assays enabled only the detection of spliced transcribed mRNA, excluding that from genomic DNA itself, by means of an exon-connection strategy by combination of a 5' PCR primer from within the mouse villin promoter sequence just upstream of the splice donor site, and the 3' primers from within the β-galactosidase gene or the villin gene. For each founder, no reporter gene expression was detected in the tissues in which villin mRNAs were not detected using the PCR assay (FIG. 4). For all founder mice, the reporter gene transcription was detected along the cephalocaudal axis of the gut (duodenum, jejunum, ileum, proximal and distal colon) following the intestine-specific expression of the villin gene (FIG. 4). In the kidney, the transgene was only transcribed in one founder of five animals obtained (FIG. 4) TFIID mRNA was present in all samples from tissues in which the reporter gene expression could not be detected (FIG. 4), confirming the quality of RNA frog these tissues.

To examine the precise cellular distribution of transgene expression within the tissues, cryostat sections of small intestine, colon and kidney were prepared and subsequently stained for β-galactosidase enzyme activity. Immunofluorescence analysis of β-galactosidase expression was also performed on the same sections and similar results were obtained with the two procedures. Sections of small intestine, colon and kidney from non-transgenic animals exhibited no detectable β-galactosidase activity. For four of five transgenic mice, a heterologous pattern of expression in small intestine and colon was observed in this assay. This heterogeneity was due to mosaicism since we examined founder animals. The expression was confined to the nucleus of the epithelial cells, as expected because the β-galactosidase gene contains a nuclear localization sequence signal (FIG. 5). The staining was detected by a stronger signal in the villin migrating cells when compared with the crypts cells, of both small intestine (FIG. 5A) and colon (FIG. 5C) epithelium, thus confirming that the −3.5 to +5.5 kb region of the mouse villin gene is able to recapitulate precisely the cellular pattern of expression, along the crypt-villus differentiation axis, of the endogenous villin gene (17). A continuous labelling of all cells of the crypt (FIGS. 5B and D) was observed, suggesting the expression of the transgene in the stem cells (10). It is noted worthy that the intensity of the β-galactosidase staining was similar to that of intestinal sections from chimeric animals Owhich possess a β-galactosidase gene integrated at the villin locus by homologous recombination procedure (32), indicating that the −3.5 to +5.5 kb region of the mouse villin gene was able to promote intestinal transcription as efficiently as the mouse villin gene itself. In the kidney of the founder mouse in which the transgene was detected by RT-PCR, the staining was only observed in the epithelial cells of the proximal tubules where the villin gene is expressed. The founder animals were able to transmit the transgene to their offspring with a similar pattern of β-galactosidase expression. In our attempt to direct an efficient expression of the reporter gene in the intestinal epithelium with shorter regulatory sequences, plasmids pA3, pB3 and pC3 were used to generate transgenic mice, because these constructs display efficient levels of β-galactosidase activity in intestine-derived CaCo2 cells.

The presence of the transgene assessed by β-galactosidase staining and immunofluorescence procedures was observed in three of the four independent lines of pA3 transgenic mice generated. These three lines expressed the reporter gene only in the small intestine (in both the immature and differentiated epithelial cells along the crypt/villus axis), and all three lines failed to express the transgene in the other tissues tested, particularly note worthy is the lack of expression in the colon and the kidney (data not shown). These results demonstrate that (i) the 3.5 kb regulatory region upstream the transcription start site of the mouse villin gene is necessary and sufficient to sustain expression strictly in small intestine of transgenic mice, (ii) the first intron of the mouse villin gene is required for colon and kidney expression in transgenic mice. Concerning the pB3 and pC3 transgenic mice, no transgene expression was observed in all tissues examined, including small intestine, colon and kidney. Thus, the key cis-acting elements of the villin gene required for intestinal and/or kidney-related expression of transgene(s) in transgenic mice are not located only within the region encompassing −480 bp upstream from the transcription start site, as observed in the cultured epithelial cells.

Discussion

In this report, we demonstrate tat cis-acting sequences located within a 9 kb region (−3.5 to +5.5 kb from the start site of transcription) of the mouse villin gene are sufficient to direct both correct tissue-specific and high expression level of the β-galactosidase reporter gene in transgenic mice, when compared with the endogenous gene (19). Reporter gene expression is detected in the whole intestinal tube and appropriately restricted to epithelial cells along the crypt-villus axis of both small intestine and colon. In addition, these regulatory elements can maintain a gradient of β-galactosidase gene expression from the crypts of Lieberkükn to tips of villi that precisely reproduce the gradient exhibited by the murine villin gene (17). Similarities between transgene and endogenous gene expression were also noticed as judged by a comparison with the staining intensity of β-galactosidase activity in intestinal sections from our transgenic mice and mice in which the reporter gene has been inserted at the natural villin locus by homologous recombination (32).

In the kidney, for only one animal of five analyzed, mouse reporter gene expression was restricted to epithelial cells of the proximal tubules recapitulating the villin expression pattern in this tissue. This suggests that transcriptional mechanisms specifying gene expression to intestine and kidney tissues are in the −3.5 to +5.5 kb region of the mouse villin gene, and that those related to kidney may be sensitive to positional effects. Indeed it is known that the transgene expression is dependent on site of chromosomal integration, and can be influenced by regulatory regions in the vicinity, presumably acting on chromatin confirmation (33). The construct lacking entirely the first intron of 55 kb, but which harboures 3.5 kb 5' to the start site of transcription of the mouse villin gene, placed in front of the β-galactosidase gene, restricts the in vivo expression of the reporter gene only into the epithelial cells along the crypt-villus axis of the small intestine. The extinction of the reporter gene expression in the kidney might be due to strong positional effects, as reported above, whereas the extinction related to the colon might be due to the absence of regulatory elements of the intron 1, such as the intestine-specific DNase I-hypersensitive site HS II. Constructs harbouring only the first 480 bp and 100 bp 5' to the start site of transcription, in combination with the lack of the first intron, placed in front of the β-galactosidase gene, both failed to drive intestine-specific and kidney-specific expression of β-galactosidase, suggesting that the intestine-specific DNase I-hypersensitive site HS IV localized just upstream from the 480 bp might play an important role in promoting reporter gene expression into the epithelial cells of the small intestine. Thus, distinct and separable regulatory elements in the mouse villin gene may direct transgene expression along the cephalocaudal axis of the gut: the regulatory elements required for transgene expression in the small intestine might be localized in the 3.5 kb region (i.e. the HS IV site) upstream from the transcription sat site, whereas those necessary for the colonic expression might be localized in the first intron (i.e. the HS II site). The inability of shorter regulatory sequences of the mouse villin gene to direct correct expression of the reporter gene in the whole intestine of transgenic mice might also be explained by spatial rearrangement of chromatin structure due to the lack of the entire first intron. In fact, the results described here are reminiscent of those of the adenosine deaminase gene (34) and the aldolase Bgene (35) in which elements located in the first intron could be required for transgene expression in vivo, because they may contain cis-acting tissue-specific enhancer elements and/or elements involved in promoting decondensation of the chromatin structure, allowing the accessibility for transcription factors and RNA polymerase.

To explain the discrepancy seen in the ability of the mouse villin gene regulatory elements to promote transcription of the reporter gene in cell cultures versus transgenic animals, we may argue that the regulation of gene expression in the intestinal epitheliums occurs as cells differentiate and migrate along the crypt-villus axis. This process depends on the contacts that these cells maintain with others neighboring cells on the one hand, and with the extracellular matrix on the other hand (36). Thus, an ex vivo system as the intestine-derived CaCo2 cell line used in the study, is limited by its weak ability in recapitulating the temporal and spatial complexities of this epithelium and emphasizes the importance to use in vivo models to define a function for specific regulatory sequences (37, 38).

Previous studies carried out in transgenic mice to map transcriptional regulatory elements responsible for intestinal expression have been performed using cis-acting sequences of genes expressed in villus associated-enterocytes of small intestine (4, 5, 38–40). In some of these cases, precocious activation in the crypts in combination with extended expression in the colon occurs in an inappropriate maimer. Thus, to our knowledge, the 9 kb regulatory region of the mouse villin gene represents the only characterized cis-acting sequences reported today that allow the expression of a heterologous gene in small intestine and colon epithelial cells of transgenic mice reproducing with great fidelity the tissue-specific and cell-specific pattern of expression when compared with that of the endogenous gene itself. In addition, the mice lines that drive a transgenic expression exclusively restricted to the intestinal mucosa could already be studied after selection of those which will not display expression into the kidney because of the positional effects.

The ability to target genes of interest in transgenic mice following the villin restricted-pattern of expression, and particularly in the crypts stem cells enables to the development of targeted genes in animal models. Experimental mouse models reproducing several steps of human colorectal carcinogenesis (a possible genetic pathway has been proposed by Fearon and Vogelstein (41)) could for instance be obtained by efficiently targeting the associated oncogenes or mutated tumor suppressor genes to colonocytes using the villin regulatory region. Another use could be in the establishment of new cell lines derived from the digestive tact by targeting a thermosensitive SV40 T antigen to the crypts resident-progenitors of intestinal cells, as used in other systems (42–44).

Several of these applications are illustrated in the proposed protocols disclosed on FIG. 8.

REFERENCES

1. Sweetser, D. A., Hauft, S. M., Hoppe, P. C., Birkenmeier, E. H. and Gordon, J. I. (1988) *Proc. Natl. Acad. Sci USA* 85, 9611–9615
2. Cohn, S. M., Simon, T. C., Roth, K. A., Birkenmeier, E. H. and Gordon, J. I. (1992) *J. Cell Biol.* 119, 27–44
3. Hermiston, M. L., Green, R. P. and Gordon, J. I. (1993) *Proc. Natl. Acad. Sci. USA* 90, 8866–8870
4. Markowitz, A. J., Wu, G. D, Birkenmeier, E. H. and Traber, P. G. (1993) *Am. J Physiol* 265, G526–G539
5. Crossman, M. W., Hauft, S. M. and Gordon, J. I. (1994) *J. Cell Biol.* 126, 1547–1564
6. Cheng, H. and Leblond, C. P. (1974) *Am. J. Anat.* 141, 461–479
7. Wright, N. A and Irwin, M. (1982) *Cell Tiss. Kinet.* 15, 595–609
8. Gordon, J. I. and Hermiston, M. L. (1994) *Curr Opin. Cell Biol.* 6, 795–803
9. Ponder, B. A, Schmidt, G. H., Wilkinson, M. M., Wood, M. J., Monk, M. and Reid, A. (1985) *Nature* (London) 313, 689–691
10. Potten, C. S. and Loeffler, M. (1990) *Development* (*Cambridge, U.K.*) 110, 1001–1020
11. Schmidt, G. H., Wilkinson, M. M. and Ponder, B. A. (1985) *Cell* 40, 425–429.
12. Hall, P. A., Coates, P. J., Ansari, B. and Hopwood, D. (1994) *J. Cell Sci.* 107, 3569–3577
13. Bry, L., Falk, P., Huttner, K., Ouellette, A., Midtvedt, T. and Gordon, J. I. (1994) *Proc. Natl. Acad. Sci. USA* 91, 10335–10339
14. Hauft, S. M., Kim, S. H., Schmidt, G. H., Pease, S., Rees, S., Harris, S., Roth, K A., Randall Hansbrough, J., Cohn, S. M., Ahnen, D. J., Wright, N. A., Goodlad, R. A. and Gordon, J. I. (1992) *J. Cell. Biol.* 117, 825–839
15. Kim, S. H., Roth, K. A., Moser, A. R. and Gordon, J. I. (1993) *J. Cell Biol.* 123, 877–893
16. Robine, S., Huet, C., Moll, R., Sahuquillo-Merino, C., Coudrier, E., Zweibaum, A. and Louvard, D. (1985) *Proc. Acad. Natl. Sci. USA* 82, 8488–8492
17. Boller, K, Arpin, M., Pringault, E., Mangeat, P. and Reggio, H. (1988) *Differentiation* 39, 51–57
18. Maunoury, R., Robine, S., Pringault, E., Huet, C., Guenet, J. L, Gaillard, J. A. and Louvard, D. (1988) *EMBO J.* 7, 3321–3329
19. Maunoury, R., Robine, S., Pringault, E., Leonard, N., Gaillard, J. A. and Louvard, D. (1992) *Development* (*Cambridge, U.K.*) 115, 717–728
20. Ezzell, R. M., Chafel, M. M. and Matsudaira, P. T. (1989) *Development* (*Cambridge, U.K.*) 106, 407–419
21. Carboni, J. M., Howe, C. L., West, A. B., Barwick, K. W., Mooseker, M. S. and Morrow, J. S. (1987), *Am. J. Pathol.* 129, 589–600
22. Moll, R., Robine, S., Dudouet, B. and Louvard, D (1987) *Virchows Arch.* 54, 155–169
23. West, A. B., Isaac, C. A., Carboni, J. M., Morrow, J. S., Mooseker, M S. and Barwick, K. W. (1988) *Gastroenterology* 94, 343–352
24. Bacchi, C. E. and Gown, A. M. (1991) *Lab. Invest.* 64, 418–424
25. Pringault, E., Robine, S. and Louvard, D. (1991) *Proc. Natl. Acad. Sci. USA* 88, 10811–10815
26. Robine, S., Sahuquillo-Merino, C., Louvard, D. and Pringault, E. (1993) *J. Biol. Chem.* 28, 11426–11434
27. Green, R. P., Cohn, S. M., Sacchettini, J. C., Jackson, K. E. and Gordon, J. I. (1992) *DNA Cell Biol.* 11, 31–41
28. Perret, C., L'Horset, F. and Thomasset, M. (1991) *Gene* 108, 227–235
29. Cohen-Tannoudji M, Robine, S., Choulika, A., Pinto, D., El Marjou, F., Babinet, C., Louvard, D. and Jaisser, F. (1998) *Mol. Cell Biol.* 18, 1444–1448
30. Breathnach, R. and Chambon, P. (1981) *Annu. Rev. Biochem.* 50, 349–83.
31. Becker, P. B. (1994) *BioEssays* 16, 541–547
32. Robine, S., Jaisser, F. and Louvard, D. (1997) *Am. J. Physiol.* 273, G759–G762
33. Cui, C., Wani, M. A, Wight, D., Kopchick, J. and Stambrook, P. J. (1994) *Transgenic Res.* 3, 182–194
34. Aronow, B. J., Silbiger, R. N., Dusing, M. R., Stock, J. L., Yager, K. L., Potter, S. S., Hutton, J. J. and Wiginton, D. A. (1992) *Mol. Cell. Biol.* 12, 4170–4185
35. Sabourin, J. C., Kern, A. S., Gregori, C., Porteu, A., Cywiner, C., Chatelet, F. P., Kahn, A. and Pichard, A. L. (1996) *J. Biol. Chem.* 271, 3469–3473
36. Hermiston, M. L. and Gordon, J. I. (1995) *J. Cell Biol.* 129, 489–506
37. Rottman, J. N. and Gordon, J. I. (1993) *J. Biol. Chem.* 268, 11994–12002
38. Bisaha, J. G., Simon, T. C., Gordon, J. L. and Breslow, J. L. (1995) *J. Biol. Chem.* 270, 19979–19988
39. Simon, T. C., Roberts, L. J. and Gordon J. I. (1995) *Proc. Natl. Acd. Sci. USA* 92, 8685–8689
40. Simon, T. C., Cho, A., Tso, P. and Gordon, J. I. (1997) *J. Biol. Chem.* 272, 10652–10663
41. Fearon, E. R. and Vogelstein, B. (1990) *Cell* 61, 759–767
42. Efrat, S., Linde, S., Kofod, H., Spector, D., Delannoy, M., Grant, S., Hanahan, D. and Baekkeskov, S. (1988) *Proc. Natl. Acad. Sci. USA* 85, 9037–9041
43. Hanahan D. (1988) *Ann. Rev. Genet.* 22, 479–519
44. Cartier, N., Lacave, R., Vallet, V., Hagege, J., Hellio, R., Robine, S., Pringault, E., Cluzeaud, F., Briand, P. and Kahn, A. (1993) *J. Cell Sci.* 104, 695–704.

What is claimed is:

1. An isolated nucleotide sequence obtained from the 5' sequence of a murine villin gene, having:
   i) a size of 9 kb on an agarose gel and comprising SEQ ID NO:1, or
   ii) a fragment within i),
   wherein said nucleotide sequence comprises nucleotide elements having a cis-regulatory activity that promotes transcription and tissue-specific expression of the murine villin gene in cells of the intestine.

2. The isolated nucleotide sequence according to claim 1, which is the sequence identified as Seq ID NO:1.

3. The isolated nucleotide sequence according to claim 1, which comprises the nucleotide fragment extending from the HS I to the HS IV Dnase I-hypersensitive sites.

4. The isolated nucleotide sequence according to claim 1, comprising a nucleotide fragment extending from the HS IV Dnase-I hypersensitive site to the translation initiation site of the murine villin gene.

5. The isolated nucleotide sequence according to claim 1, which comprises a nucleotide fragment extending from the nucleotide at position −100 upstream from the transcription initiation site, to the translation initiation site.

6. The isolated nucleotide sequence according to claim 1, which comprises a nucleotide fragment extending from the nucleotide at position −480 from the transcription initiation sequence, to the translation initiation site.

7. The isolated nucleotide sequence according to claim 1, which is the sequence extending from the translation initiation site of said murine villin gene upstream to a sequence that is 3.5 kb upstream from the transcription initiation site of said murine villin gene, provided the intron 1 region, located between said sites, is deleted or deleted in part.

8. The isolated nucleotide sequence according to claim 1, which is mutated by deletion of one or several nucleotides, within the nucleotide fragment of 5.5 kb corresponding to the intron 1 region extending from position 47 starting from the transcription initiation site, provided that said mutation does not affect the presence of the HS II Dnase I-hypersensitive site.

9. The isolated nucleotide sequence according to claim 1, which comprises nucleotide regions having a regulatory activity affecting the level of expression of the murine villin gene.

10. The isolated nucleotide sequence according to claim 1, which is obtained from the nucleotide sequence of the murine villin gene having a size of 9 kb on an agarose gel and extending 3.5 kb upstream from the transcription initiation site and 5.5 kb downstream from said site, or a fragment thereof, said nucleotide sequence or fragment thereof having a regulatory activity on the level of expression of the murine villin gene in transgenic mice.

11. An isolated nucleotide sequence obtained from the 5' sequence of a murrine villin gene having
   i) a size of 9 kb on an agarose gel and is the sequence identified as SEQ ID NO:1; or
   ii) a fragment of i), wherein said fragment is selected from the group consisting of
      (a) a nucleotide fragment extending from the translation initiation site of said murine villin gene upstream to a sequence that is 3.5 kb upstream from the transcription initiation site of said murine villin gene, provided the intron 1 region located between said sites is deleted;
      (b) a nucleotide fragment extending from the HS I to the HS IV Dnase-I hypersensitive sites;
      (c) a nucleotide fragment extending from the HS IV Dnase-I hypersensitive site downstream to the translation initiation site of the murine villin gene;
      (d) a nucleotide fragment extending from the nucleotide at position −100 upstream from the transcription initiation site to the translation initiation site; and
      (e) a nucleotide fragment extending from the nucleotide at position −480 from the transcription initiation sequence to the translation initiation site;
   wherein said nucleotide sequence comprises nucleotide elements having cis-regulatory activity that promote the transcription of the murine villin gene.

12. An isolated nucleotide sequence obtained from the 5' sequence of a murine villin gene which is the sequence extending 3.5 kb upstream and 5.5 kb downstream from the transcription initiation site of the murine villin gene.

13. An isolated nucleotide sequence obtained from the 5' sequence of a murine villin having
   i) a size of 9 kb on an agarose gel and is the sequence identified as SEQ ID NO:1; or
   ii) a fragment of i), wherein said fragment is selected from the group of:
      (a) a nucleotide fragment extending from the translation initiation site of said murine villin gene upstream to a sequence that is 3.5 kb upstream from the transcription initiation site of said murine villin gene, provided the intron 1 region is located between said sites is deleted;
      (b) a nucleotide fragment extending from the HS I to the HS IV Dnase-I hypersensitive sites;
      (c) a nucleotide fragment extending from the HS IV Dnase-I hypersensitive site downstream to the translation initiation site of the murine villin gene;
      (d) a nucleotide fragment extending from the nucleotide at position −100 upstream from the transcription initiation site, to the translation initiation site; and
      (e) a nucleotide fragment extending from the nucleotide at position −480 from the transcription initiation sequence, to the translation initiation site;
   wherein said isolated nucleotide sequence comprises nucleotide elements having a cis-regulatory activity that promotes the transcription of the murine villin gene and comprises nucleotide regions having a regulatory activity affecting the level of expression of the murine villin gene.

14. An isolated nucleotide sequence obtained from the 5' sequence of a murine villin gene, having:
   i) a size of 9 kb on an agarose gel and is the sequence identified as SEQ ID NO:1; or
   ii) a fragment within i), wherein said isolated nucleotide sequence comprises nucleotide elements having a cis-regulatory activity that promotes the transcription and tissue-specific expression of the murine villin gene in intestine epithelial cells and kidney proximal tubules.

15. The isolated nucleotide sequence according to claim 14, which comprises nucleotide regions having a regulatory activity affecting the level of expression of the murine villin gene.

16. An isolated nucleotide sequence obtained from the 5' sequence of a murine villin gene having;
   i) a nucleotide fragment extending from an HS IV Dnase I-hypersensitive site downstream to the translation initiation site of the murine villin gene and extending 3.5 kb upstream of the transcription initiation site of SEQ ID NO:1; or
   ii) a fragment within i), wherein said isolated nucleotide sequence comprises nucleotide elements having a cis-regulatory activity that promotes the transcription and tissue-specific expression of the murine villin gene in intestine epithelial cells and kidney proximal tubules.

* * * * *

SEQUENCE LISTING

<160> NUMBER OF SEQ ID NOS: 20

<210> SEQ ID NO 1
<211> LENGTH: 8995

-continued

```
<212> TYPE: DNA
<213> ORGANISM: Mus musculus
<220> FEATURE:
<221> NAME/KEY: intron
<222> LOCATION: (3489)..(8981)
<221> NAME/KEY: exon
<222> LOCATION: (3443)..(3487)
<223> OTHER INFORMATION: exon 1

<400> SEQUENCE: 1
```

| | | | | | |
|---|---|---|---|---|---|
| gatctggtgc | accaaggaca | ctgtggtccc | agcactgggg | aggtggaggg | aggagggtca | 60 |
| gaagtttaag | gtcatccttg | gttacatagc | aaggtttcag | ccagcttcag | ctacatgaaa | 120 |
| cctttgtttg | tttgtttgtt | tgttttaaag | cattaataaa | taataccata | aggaggttgg | 180 |
| cagtggtggc | agacaccttt | aattccagta | ttcaggaggc | agaagcaggc | agatctctgt | 240 |
| gagttcgaag | tcagcctagt | ctgcaaagct | agttccagga | tggcaagggc | tacacagaga | 300 |
| aaccttgtct | cataaaacca | aagtagtagt | agtagtagta | atgccataga | gaaaattgga | 360 |
| gtccattcag | gatggaccat | cctataagat | gattctcttg | acccaggtaa | gctaatgtca | 420 |
| tggggaaagg | ggatgggact | gtcctagatt | aaaaagtgct | gaggcgatgc | ctattctcaa | 480 |
| tttgattcca | tatgaaaagg | ctgataaggc | ccaagagaag | tggaactggg | actctggact | 540 |
| gaagacgtga | cggccttata | aacactggca | cttataaaca | cttataaaca | ctggcacagg | 600 |
| cgttcaggtt | tgaagatcac | tttcaaacca | cagaacagaa | agtgctcgct | cgtcctcagc | 660 |
| gtagcgagca | ctggctgcag | aagagtgata | tttagtgaaa | gctaccttca | caatatcttt | 720 |
| gcacttatca | catacacgtg | tcaaatgtgc | taactcccta | gtccacagat | ggctgttaca | 780 |
| ctcgtttctg | ctttcccatc | tggttgacat | ttgtcagaac | cagaaattag | aaatgtgggt | 840 |
| atttatttgt | gtgctgagga | caccatccag | ggcttttcac | atttcaggca | catggtttac | 900 |
| taactgggct | acttctccaa | cggttttgaaa | ccatttgttt | tatatttact | tattttgtgt | 960 |
| gcatgaggta | ggcatgtata | cgtatgtata | ggagtcatgc | atgtggctgc | taccctcaaa | 1020 |
| atcattgcag | atccccagca | agtgaagtca | ccgagcgttg | taagttgtta | tgtgggactg | 1080 |
| ggagccaagg | ctgggttctc | tgcaagagca | gccagtggcc | ttaaccatgg | gaccagctct | 1140 |
| ctaggcctaa | ggtaatcttt | agttttttaa | aaatatatat | tctcagccgg | gtgtggtggc | 1200 |
| acacgccttt | aatcccagca | cttgagaggc | tgaggtgtag | gaattataca | cacaggccag | 1260 |
| ctggggtgca | gagcttggcc | ctgtttttttt | tgttttttct | ttatgtgcac | tggtgtctta | 1320 |
| cctgcgtgta | tgtccgtgca | agggtgtcag | atcccttgga | gctggagtta | aagacagttg | 1380 |
| tgatcacgct | gccgttacag | atgctggaaa | ttgaacccag | gtgtccctag | agaagcagcc | 1440 |
| agtgctctta | acttctgagc | cacccctcca | accctgcttt | tagagactct | taaccttttg | 1500 |
| tgtaatgtgg | gaactgagtg | gatcttgcac | ttaccaagtg | tgtgctgcgc | tgtagcatca | 1560 |
| ctgagcccgt | acccacacga | ctagtggata | cagtttaagg | gcaaacactt | aacaatgaca | 1620 |
| atagttggat | agagtttgaa | tatagtcctg | agctattggt | tagcgtgacc | tttgctgtcc | 1680 |
| ttagcatgtg | ctgtgagaag | atagaaaaat | gaagacttga | gtctagtcct | ggaacccaca | 1740 |
| gaggcaggcg | agaacccact | cctgaaagtt | gttctctgag | cttcacatac | aacttcacat | 1800 |
| aatagttaca | atgataataa | taattagtaa | attcttttaa | aaggtatatg | ttgggaggga | 1860 |
| gagatggctc | agcttccagg | agcacttgct | gctcttgcag | aggacctaga | ttcagttccc | 1920 |
| aggactcata | tggtggctca | cagccatctg | taaatccagt | tccagagggt | tccacaccct | 1980 |
| cttctggcct | ccacaggcac | cacatacata | gtacacagac | atacatgcag | gcaaaacacc | 2040 |

-continued

```
catacacaca taaataaata aggaaactta aaggtgcat gtgttggtaa acattgtgct      2100
tacacatgct gattgaagac atgtacaacg cacacactga agagggatct ggggctggag      2160
agatggctca gcggttaaga gcactgactg ctcttccgaa ggaaggtcct gagttcaaat      2220
cctagcaacc acatggtggc tcacaaccat ccataatgag atctgacacc ctcttctggt      2280
gcatctgaag acagctgcag agctacagtg tacttagata tactaataaa taaatctttt      2340
tttaaaaaaa tgaagaggga tctgagacac ctcaaaagag attatgagca gtgactcacg      2400
ggtgattatc tatcctggag ttttttcctt ccgcttggct tgcaactggg tggacagacg      2460 cccctttca ttcacaagaa cgggtgctac attatttctg aacaaaacag cacctgcagt      2520
atgtttactg tccttgctga ctatgagcac gcgcacgcgc gcgcgcacac acacacacac      2580
acacacacac acacacacac acacacacac attcagtctc cagagctctt gggaaggtca      2640
agaagaggct gccctcaaac cgatcttca tctttccctc ctaaaggaga ccacgattcc       2700
aaggtggcag aagatctaca gggggcagag gcagggaggg ggaagcaggc catggtttcc      2760
agagacctac agcagagggc agcaaggcag atccccaggt ccagggcagg gaggtggagg      2820 ccccttgttcc gaggagaagg caggcggcag aacaggggttc aaaggcacag gtttatggca     2880
gctcataaaa gtggaggtcg tggctcactc agaaaggagg aagaagggaa aggcccttgt      2940
gcccactgag cgagggtcat gctgagtagg agagatctgc aggggtgcca ggagccccac      3000
ctgtctgtcc caagggaacc ccaagtgtga actctggcct tgggtgctga gttccagcta      3060 caagaccccca ggagtcctac tccatcccca tccagtgccc cctcgccccg ccacaccccca     3120 cccccgactc ccgtgccact tctctagggc tggagggtgg ccagccctgg tgggggttgc      3180
ctacctgcag gtagagccca ggtcctagcc ggaagtgcac cccatccctg aagctgcaga      3240
gccaagggcg gggcacacgg cagctcaggc tgtcaggctg ttgctgggct ctaggttccc      3300 aggggacctgg gcacctactt ccccaccccc ccatccattc tctctggggc cctatcttcc      3360
cttatatggt gaaggaagtt cctggggggg ggggtggtg gtgaggacaa aggtcgttcg      3420
gtctcctgca gccagcttgc ca caa ctt cct aag atc tcc cag gtg gtg gct      3472
gcc tct tcc aga cag gtaaggcaat tgggtgggga cacatggtga ccacaggtgg       3527
ttggagggga cagggtcctt gcttctctct ggcagcctgt gctttctgta gccacttggt     3587 ataagttttgg gggtgaggta aggtgctctg aaactctgaa agaagcaaga agccagcagg    3647
ctgtctgggg ccttcaatga aggaagttca cagaccccct ttcctgtaag tcaccttcgc      3707
ttcatctgtg tagattccct gggaccaagg tggctcctgg gactcagatt tctacaatta     3767
aaatcaggac agtcctgaga cttggactcc gtgcctgtat ttactacttc tctctggctg     3827
ctcatttctg tgttcatgtc ttacacatct gaaatggttt ctttgtgtca ccattcccct      3887
gacactcctg ggaggtcgta tccttggcac atgtatcctg ggatgtaagc tgcagccacc     3947
aggagagagg gggagagtca ggagctgtgt cctaggccct attaggcctg acatcaccc      4007 ctttcctaga aatggcccct ccattttccg gttaccatga tctatttat atcagagtgg      4067 gcagtgaaag ccaaacctgc ccagaagttt gggactcact cagaccaagg ttatctgctc     4127
agaaatcccc ctgtcacttg aggttgggag aatctgcctc tgggggcttc caggtcttgg     4187
ttagcaggag ggtatccttt gtatagggca tgacctagtc tatggtgtta ctacattcct     4247
gtccagttaa aagctggaac taaaacccac ggcagcgccc aggattctct acagttgtac     4307
cccaagaaca acaagacagt agatatgcaa ggataggtag ctggggagaa gaagaactta     4367
aaccccccca aaggcccaca ggttccgttc cctagttcac aatgccagta tgagtgctag    4427
```

```
ctactatggg ctgtgagttg gtagctacaa gcatgagtga tgttcatgtg tgtagtgtgt      4487
ataatctgag cacttgggag gctgaagcag gaggattgct atatgtttga ggccagcctg      4547
agctatagag cgagactttg tctttaagaa aaaaatgaaa gcccagcagt ggtggcacac      4607
gcctttaatc ccagcacttg ggaggcagaa gcaggcagat ttctgagttc aaggccagcc      4667
tggtctatag agtgagttcc aggacagcca gggctacaca gagaaaccct gttttgaaaa      4727
accagaaaaa caaacaaaa caaacaaaa caaacccaa acccaaaccc aaacctctca        4787
tctctcatct ctctaggctg tgtctgtcta ggtggtagag tttggggact tcagacttat      4847
atataaatag gccttttat cactggtcag agacgagaaa ggtttcagtc tgggacacag      4907
tgggaccctg agaaagtact ccttgccagc ccaaaaattc tgggaaggct tcctggagga      4967
agtgtgtccc gatcagacta ctgttctaga aggcagaaga gagggttgga agaatgttgg      5027
tggacagaca gttggaacag aaggacagga gggggaggca tccaagattc tgaacatgta      5087
gctgactttt ggttctctgg gtgacaagtg tcccccaggg atagggctgt agaaagggga      5147
ccaggggtga gccaatgagt tcaagttgag ggacacatcc agcccagggt ccttgctggc      5207
aagctaaaga atgagagccc tctaaccctc cctgaagttt aggggagaca ggagagctga      5267
ggagatcctt ctagggtgaa ggagaggtat ctgctctgac caacatggct aggagcagaa      5327
gcagttggac cagttacccc tcagaaccag ccatcccctc ttggctctaa ggaggctggg      5387
cccctttctg tttaagaatc ttacttttct tcagagagag gcagcaagcc tttgtcccct      5447
ccctgttggt caataaacac ccctgtgtgt aacattagtt tattttactg tcagtttgct      5507
ccaggacagt ccatctggta gacctctgct cctaactcac caaggtatgg cccacattcc      5567
tcacccagaa gagtgcagaa gagagcctta gagaaagggt aacagtaaca agatggcca      5627 gaataaaaca aaaactacta tcctttgtac ccaaattggt tttgctgaac caggaggggg      5687
tgtgtgagtg tatgtgtgtg tgtgtgtgtg tgtgtgtgtg tgtgtgtgtg tgtgtgtgtg      5747
tgtgtgtgtg tgtcttgggg gacttttcat gctaaagaat atctgatatt ggcgcccatg      5807
ccaacagggg tattgtgggag agtcaggctt ctgcaaacac agtaagctgc caagatgga      5867 ttggtggcct gaatcaccaa ggggcaggct gatcagagtg gacagaacat cacaagataa      5927
gccaccctgt ggggctcaga agagggagtt tacaagaggt aaaggccaag ccatttatta      5987
tccaagacat gactcaaaat caaagtgcaa ggagagatta gctggagaga tggggctgtc      6047
agtgtgggac acctgacctt gcacttatta gtcactaggc caaggagcag tcacagaggg      6107
tgactgggtc ctactcagct tggagcaggc acgtggagaa tgggtgacct ccatcctgat      6167
ggagagggct gagcaccacc aggtacaagt gttccctgtg tctcatgcca ggattcctgg      6227
ccagttttca aaggactaag gactcatctc tggtggaaac aaagtatcca agccctaagc      6287
cccattttgg tctaattaaa tcagaacccc tggggatgca ggctctgagc agcaggagct      6347
ttttaaaaag ctcccaggtg attctgatca gcagctggaa caaacacagc tacaggttca      6407
aacagaaaga ggcaaagcta gggaaagctt gggatgggga gccttcttcc aggccagtag      6467
atggaggctg gttagcagtg gtggcagctt ctctctgcct gtcatatagc tatccatcca      6527
ctcatccatc catacaccca cccatccatt tatgcaccca tccttccatc catccatcta      6587
tccagctacc cacccacgca tccatccaaa ccttcctttt ctccttcttt ctttcttttt      6647
tccttcactc attcatttat ccaacagaga actggtattg tactaaatgt gggagattta      6707
attaattttt agaagctctg ttgattgact gattgtgcat gtatgtggac aggtacatac      6767
cacagcacac gtgtggcaat cggagaaagg ttttgggtgt tgttttctct tcccaccgtg      6827
```

-continued

```
tgggttctgg ggattgaact caaattatcg ggctggtggc aagtgtctt  accaccgagc    6887 cattttgctg acacatcatt attattagaa agcatcttat gtagtccagg ctggcctcaa    6947
gcttgctatg tcgccacgga tgacctttaa ctcctgctct tccagcctcc acccgagtgc    7007
taggtttaca ggtgttcaac tggtgaatgc ctttaatccc agcactctgt ggggggggggg   7067 ggggaggcgg atccctgagt tggaggccag tttggtctac agagtttcag gatacctggg    7127
gctatacagg gaaaccctat cccaaacaaa caaacaaaca aacaaaaaat attctgtgca    7187
ataatcacag agattagagg atattagtag ggtagtaggg ctggtgaggg agagtcatgc    7247
tttcttttgt attataatag taaagtactc acaagatgca ttatctatct atctatctat    7307
ctatctatct atctatctat ctatctacct acctacctac ctatccatcc atccatctat    7367
cgtatagccc aggctgcttt gactctgaat gctcctattt ctgggtcaac tcttcacccc    7427
tagtgttggg tttaccaaca cccagacatt tatttattt tgttttattt tattaatcta     7487
ggagctcagg gtgggactca gggtcttgtg catgctaagc aagctctctg ccacagagct    7547
gcagctccag tccccatttt gttcaggtga ctctgtgaca gttgtcatat tcgcagcgct    7607
atgtagctct ctccacctcc cagttccagc actttctggt catcccagtg ggcgggcaac    7667
tctgtgctca ccagtgccct gttccctgtc ttcagaccta catatttgcc tgtctgaaca    7727
gttcatgtaa atgggatgcg ttcctgtgta ttcttttatg gctggcccct ttatcttagc    7787
acagtttgtg ttgggccatg tgtcactgct atactctatc ttatcatcat cttatggctt    7847
aatagtgttc ctttgtgtgg ataaaccact ttctgtttca tttactgatg gaaatttgtg    7907
gccccacccc cacccttttt ttttttattt gagacaaggt cttcctgtgt aatcttgcaa    7967
tcttggctgt cctgagctca ctctgtagac caggctgtga ggctgtcctt ccactttga    8027 cactcctgtg aacagagtag ccatgaactt caaagacaat tttctgtttt ggtttgtttt    8087
ttacatttgt gtgtgtatgc gtgtatatgt gcatgttgt gtcttcaggt gctcacatgt     8147
gtgtacctgt gtgtgggaca gagaacaaac cgatgtgcca ttcctcagat actacgcatc    8207
ttgttaatat gtatgtatta tgtatgttta tttagtgtgc ccaagtatgc aggtatttg     8267 ttggagtttt caccttccct tgtgggctct ccgcattaaa ctcagctcct cgggctagtg    8327
agcaatgcct tcactcgatg agccatctcg ctgcccctgc tgccacctcc tcctatttc    8387 ccagatggga ctacgcactg cactggccta aagctcacca agtcatccag agtggctagc    8447
cagggagact cagggatatg ctggcctctg cctccacagt gctagaatta caggcataca    8507
tcactgctgg aagattttta acctgaatcc tgaggataga gcaggcactc taccaatgga    8567
gggttctttt tgtgtttggt ttggttccct ctgcataaga tcaggcagtc tgaaatagtg    8627
tagcctgggc tacataacat cttgtctcaa aaagcctata gaggtaggga ggtcgaggct    8687
aaagaagagc cttaagccgg ctgtgatagc acacaggata gcctgcacta tatagcaaga    8747
ccttgtttca aaaacatgga gggagggta tgttttaagt gctgggctgt gtaacaggca     8807
ctaagggagc caatgtagac atttgactaa gaaaggatca tcatcaaagc cgggtgggca    8867
gggtagaggt tggactacag tggtcaagac ccccatagga agccagtttc ccttcttcct    8927
ctgggcctca agcctggctc gacggccact gctctcacat gccttctcct ctaggctcgt    8987
ccaccatg                                                             8995
```

<210> SEQ ID NO 2
<211> LENGTH: 23
<212> TYPE: DNA

```
-continued

<213> ORGANISM: Artificial Sequence
<220> FEATURE:
<223> OTHER INFORMATION: oligonucleotide

<400> SEQUENCE: 2
gagtggtgat gttgagagag cct                                           23

<210> SEQ ID NO 3
<211> LENGTH: 18
<212> TYPE: DNA
<213> ORGANISM: Artificial Sequence
<220> FEATURE:
<223> OTHER INFORMATION: oligonucleotide

<400> SEQUENCE: 3
catagttctc gttccggt                                                 18

<210> SEQ ID NO 4
<211> LENGTH: 44
<212> TYPE: DNA
<213> ORGANISM: Artificial Sequence
<220> FEATURE:
<223> OTHER INFORMATION: oligonucleotide

<400> SEQUENCE: 4
gatctcccag gtggtggctg cctcttccag acaggctcgt ccac                    44

<210> SEQ ID NO 5
<211> LENGTH: 44
<212> TYPE: DNA
<213> ORGANISM: Artificial Sequence
<220> FEATURE:
<223> OTHER INFORMATION: oligonucleotide

<400> SEQUENCE: 5
catggtggac gagcctgtct ggaagaggca gccaccacct ggga                    44

<210> SEQ ID NO 6
<211> LENGTH: 18
<212> TYPE: DNA
<213> ORGANISM: Artificial Sequence
<220> FEATURE:
<223> OTHER INFORMATION: oligonucleotide

<400> SEQUENCE: 6
caacttccta agatctcc                                                 18

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
attcaggctg cgcaactgtt                                               20

<210> SEQ ID NO 8
<211> LENGTH: 24
<212> TYPE: DNA
<213> ORGANISM: Artificial Sequence
<220> FEATURE:
<223> OTHER INFORMATION: oligonucleotide

<400> SEQUENCE: 8
gcaacagtcg ctggacatca cagg                                          24
```

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
ccacggacaa ctgcgttgat                                           20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
ggctcatagc tactgaactg                                           20

<210> SEQ ID NO 11
<211> LENGTH: 31
<212> TYPE: DNA
<213> ORGANISM: Artificial Sequence
<220> FEATURE:
<223> OTHER INFORMATION: oligonucleotide

<400> SEQUENCE: 11
ccacaacttc ctaagatctc ccaggtggtg g                              31

<210> SEQ ID NO 12
<211> LENGTH: 31
<212> TYPE: DNA
<213> ORGANISM: Artificial Sequence
<220> FEATURE:
<223> OTHER INFORMATION: oligonucleotide

<400> SEQUENCE: 12
ctgcctcttc cagacaggct cgtccaccat g                              31

<210> SEQ ID NO 13
<211> LENGTH: 12
<212> TYPE: DNA
<213> ORGANISM: Artificial Sequence
<220> FEATURE:
<223> OTHER INFORMATION: oligonucleotide

<400> SEQUENCE: 13
ctaggcggcc gc                                                   12

<210> SEQ ID NO 14
<211> LENGTH: 17
<212> TYPE: DNA
<213> ORGANISM: Artificial Sequence
<220> FEATURE:
<223> OTHER INFORMATION: oligonucleotide

<400> SEQUENCE: 14

```
catgacgtcg gacttgc                                              17
```

<210> SEQ ID NO 15
<211> LENGTH: 17
<212> TYPE: DNA
<213> ORGANISM: Artificial Sequence
<220> FEATURE:
<223> OTHER INFORMATION: oligonucleotide

<400> SEQUENCE: 15

```
ggccgcaagt ccgacgt                                              17
```

<210> SEQ ID NO 16
<211> LENGTH: 27
<212> TYPE: DNA
<213> ORGANISM: Artificial Sequence
<220> FEATURE:
<223> OTHER INFORMATION: oligonucleotide

<400> SEQUENCE: 16

```
tgcaaaagta ctgaatataa acttgtg                                   27
```

<210> SEQ ID NO 17
<211> LENGTH: 30
<212> TYPE: DNA
<213> ORGANISM: Artificial Sequence
<220> FEATURE:
<223> OTHER INFORMATION: oligonucleotide

<400> SEQUENCE: 17

```
atttgcggcc gctttacata attacacact                                30
```

<210> SEQ ID NO 18
<211> LENGTH: 31
<212> TYPE: DNA
<213> ORGANISM: Artificial Sequence
<220> FEATURE:
<223> OTHER INFORMATION: oligonucleotide

<400> SEQUENCE: 18

```
gggtaccatg gataaagttt taaacagaga g                              31
```

<210> SEQ ID NO 19
<211> LENGTH: 30
<212> TYPE: DNA
<213> ORGANISM: Artificial Sequence
<220> FEATURE:
<223> OTHER INFORMATION: oligonucleotide

<400> SEQUENCE: 19

```
ggaattcggc gccgcagtag caatcaaccc                                30
```

<210> SEQ ID NO 20
<211> LENGTH: 12
<212> TYPE: DNA
<213> ORGANISM: Artificial Sequence
<220> FEATURE:
<223> OTHER INFORMATION: oligonucleotide

<400> SEQUENCE: 20

```
ctaggcggcc gc                                                   12
```